United States Patent [19]
Martin et al.

[11] Patent Number: 5,225,212
[45] Date of Patent: Jul. 6, 1993

[54] MICRORESERVOIR LIPOSOME COMPOSITION AND METHOD

[75] Inventors: Francis J. Martin, San Francisco; Martin C. Woodle, Menlo Park; Carl Redemann, Walnut Creek; Annie Yau-Young, Palo Alto; Ramachandran Radhakrishnan, Fremont, all of Calif.

[73] Assignee: Liposome Technology, Inc., Menlo Park, Calif.

[21] Appl. No.: 624,548

[22] Filed: Dec. 10, 1990

Related U.S. Application Data

[63] Continuation-in-part of Ser. No. 425,224, Oct. 20, 1989, Pat. No. 5,013,556.

[51] Int. Cl.⁵ .................... A61K 9/127; A61K 31/765
[52] U.S. Cl. .................... 424/450; 424/426; 424/78.31
[58] Field of Search .................... 260/403; 424/450; 428/402.2; 264/4.1, 4.3, 4.6

[56] References Cited

U.S. PATENT DOCUMENTS

| | | | |
|---|---|---|---|
| 4,426,330 | 1/1984 | Sears | 260/403 |
| 4,534,899 | 8/1985 | Sears | 260/403 |
| 4,837,028 | 6/1989 | Allen | 260/403 |

FOREIGN PATENT DOCUMENTS 118316 12/1984 European Pat. Off. .

Primary Examiner—Thurman K. Page
Attorney, Agent, or Firm—Peter J. Dehlinger

[57] ABSTRACT

A liposome composition for extended release of a therapeutic compound into the bloodstream. The liposomes are composed of vesicle-forming lipids and between 1–20 mole percent of a vesicle-forming lipid derivatized with hydrophilic polymer, have sizes in a selected size range between 0.1 and 0.4 microns, and contain the therapeutic compound in liposome-entrapped form. The dosage form of the composition contains at least about three times the dose of the compound required for intravenous injection in free form. Also disclosed in a method for extending to at least 24 hours the period in which an intravenously administered therapeutic compound is therapeutically active in the bloodstream, and novel liposomes compositions for practicing the method.

26 Claims, 12 Drawing Sheets

MICRORESERVOIR LIPOSOME COMPOSITION AND METHOD

This application is a continuation in part of copending application Ser. No. 425,224, filed Oct. 20, 1989 issued May 7, 1991, as U.S. Pat. No. 5,013,556.

FIELD OF THE INVENTION

The present invention relates to a liposome composition and method for administering a therapeutic compound into the bloodstream over an extended period.

REFERENCES

Allen, T. M., (1981) Biochem. Biophys. Acta 640. 385397.
Allen, T. M., and Everst, J. (1983) J. Pharmacol. Exp. Therap. 226. 539–544.
Ashwell, G., and Morell, A. G. (1974) Adv. Enzymology 41, 99–128.
Banga, A. K., et al., Int J Pharm, 48:15 (1988).
Czop, J. K. (1978) Proc. Natl. Acad. Sci. U.S.A. 74:3831.
Durocher, J. P., et al. (1975) Blood 45:11.
Ellens, H., et al. (1981) Biochim. Biophys. Acta 674:10–18.
Gabizon, A. Huberty, J. Straubinger, R. and Papahadjopoulos, D. (1988-1989) J. Liposome Resh. 1, 123–135.
Gregoriadis, G., and Ryman, B. E. (1974) Eur. J. Biochem. 24, 485–491.
Gregoriadis, G., and Neerunjun, D. (1974) Eur. J. Biochem. 47, 179–185.
Gregoriadis, G., and Senior, J. (1980) FEBS Lett. 119, 43–46.
Greenberg, J. P., et al (1979) Blood 53:916.
Hakomori, S. (1981) Ann. Rev. Biochem 50, 733–764.
Hwang, K. J., et al. (1980) Proc. Natl. Acad. Sci. U.S.A. 77:4030.
Jonah, M. M., et al. (1975) Biochem Biophys. Acta 401, 348.
Juliano, R. L., and Stamp, D. (1975) Biochem. Biophys Res. Commun. 63. 651–658.
Karlsson, K. A. (1982) In: Biological Membranes, Vol. 4, D. Chapman (ed.) Academic Press, N.Y., pp. 1–74.
Kimelberg, H. K., et al. (1976) Cancer Res. 36,2949–2957.
Lee, K. C., et al., J. Immunology 125:86 (1980).
Lee, V. H. L., Pharm Int, 7:208 (1986).
Lee, V. H. L., Biopharm Manuf, 1:24 (1988).
Lopez-Berestein, G., et al. (1984) Cancer Res. 44, 375–378.
Okada, N. (1982) Nature 299:261.
Poste, G., et al., in "Liposome Technology" Volume 3, page 1 (Gregoriadis, G., et al, eds.), CRC Press, Boca Raton (1984);
Poznansky, M. J., and Juliano, R. L. (1984) Pharmacol. Rev. 36. 277–336.
Richardson, V. J., et al. (1979) Br. J. Cancer 40, 3543.
Scherphof, T., et al. (1978) Biochim. Biophys. Acta 542, 296–307.
Senior, J., and Gregoriadis, G. (1982) FEBS Lett. 145, 109–114.
Senior, J., et al. (1985) Biochim. Biophys. Acta 839, 1–8.
Szoka, F., Jr., et al. (1978) Proc. Natl. Acad. Sci. U.S.A. 75:4194.
Szoka, F., Jr., et al. (1980) Ann. Rev. Biophys. Bioeng. 9:467.
Woodruff, J. J., et al. (1969) J. Exp. Med. 129:551.

BACKGROUND OF THE INVENTION

With recent advances in biotechnology, the development of medicinal peptides or proteins has become an integral part of the pharmaceutical industry (Lee, 1986, 1988). Several therapeutic proteins have been successfully produced through recombinant DNA technology, such as human growth hormone, human insulin, $\alpha$-interferon, interleukin-2, TPA, and a variety of peptide vaccines, all of which are now commercially available (Banga). As oral administration generally does not result in therapeutic responses, the parenteral route is preferred However, when administered parenterally, most peptides and proteins have an extremely short half-life in the bloodstream, typically less than 2 hours, and thus require large doses and multiple daily injections or infusions. Often, the therapeutic regimens employed require close medical supervision and are difficult for most patients to accept.

Liposomes have been proposed as a carrier for intravenously (IV) administered compounds. However, the use of liposomes for slow release of liposome-entrapped material into the bloodstream has been severely restricted by the rapid clearance of liposomes from the bloodstream by cells of the reticuloendothelial system (RES). Typically, the RES will remove 80–95% of IV injected liposomes within one hour, and effectively remove circulating liposomes from the bloodstream within of 4–6 hours.

A variety of factors which influence the rate of RES uptake of liposomes have been reported (e.g., Gregoriadis, 1974; Jonah; Gregoriadis, 1972; Juliano; Allen, 1983; Kimelberg, 1976; Richardson; Lopez-Berestein; Allen, 1981; Scherphof; Gregoriadis, 1980; Hwang; Patel, 1983; Senior, 1985; Allen, 1983; Ellens; Senior, 1982; Hwang; Ashwell; Hakomori; Karlsson; Schauer; Durocher; Greenberg; Woodruff; Czop; and Okada). Briefly, liposome size, charge, degree of lipid saturation, and surface moieties have all been implicated in liposome clearance by the RES. However, no single factor identified to date has been effective to provide long blood halflife, and more particularly, a relatively high percentage of liposomes in the bloodstream than 1 day or more after IV administration.

One factor which does favor longer liposome lifetime in the bloodstream is small liposome size, typically in the size range of small unilamellar vesicles (SUVs): 0.03–0.07 microns. However, the intravesicular volume of SUVs is quite limited, to the extent that loading SUVs with a peptides or proteins in a therapeutically effective dose range is not practical for parenteral administration.

SUMMARY OF THE INVENTION

It is therefore one general object of the invention to provide a liposome composition and method for administering a therapeutic compound for an extended period in the bloodstream.

The invention includes, in one aspect, a liposome composition effective to extend to at least 24 hours, the period of effective activity of an therapeutic compound which can be administered intravenously in a therapeutically effective amount, and which has a blood halflife, in free form, of less than about 4 hours. The composition includes liposomes (i) composed of vesicle-forming lipids and between 1–20 mole percent of a vesicle-forming lipid derivatized with a biocompatible hydrophilic polymer, and (ii) having a selected mean particle diameter in the size range between about 0.1 to 0.4 microns, and the compound in liposome-entrapped form. The composition is intended for intravenous administration at a dose which contains an amount of the liposome-entrapped compound which is at least three times the therapeutically effective dose for the compound in free form.

In one preferred embodiment, the hydrophilic polymer is polyethyleneglycol having a molecular weight between about 1,000–5,000 daltons, and the polymer is derivatized with the polar head group of a phospholipid, such a phosphatidylethanolamine (PE). Alternatively, the polymer may be other suitable biocompatible hydrophilic polymers, such as polylactic acid and polyglycolic acid.

Also in one preferred embodiment, the composition is effective to extend to at least 48 hours, the period of therapeutic activity of an intravenously injected polypeptide which can be administered intravenously in a therapeutically effective amount. The polypeptide may be a peptide or protein, such as superoxide dismutase, glucocerebrosidase, asparaginase, adenosine deaminase, interferons (alpha, beta, and gamma), interleukin (1,2,3,4,5,6,7), tissue necrosis factor (TNF - alpha, beta), colony stimulating factors (M-CSF (macrophage), G-CSF (granulocyte), GM-CSF (granulocyte, macrophage), TPA, prourokinase, and urokinase, HIV-1 vaccine, hepatitis B vaccine, malaria vaccine, and melanoma vaccine, erythropoietin (EPO), factor VIII, bone growth factor, fibroblast growth factor, insulin-like growth factor, nerve growth factor, platelet-derived growth factor, tumor growth factors (alpha, beta), somatomedin C (IGF-1), and a ribosome inhibitor protein, which is therapeutically active when administered intravenously. Where the polypeptide is active in the picogram/ml range, such as is vasopressin, the composition is effective to deliver a therapeutically effective amount of the peptide into the bloodstream for a period of between 5–10 days.

Also forming part of the invention is a method for extending to at least 24 hours, the period of effective activity of an therapeutic compound which can be administered intravenously in a therapeutically effective amount, and which has a halflife in the blood, in free form, of less than about 4 hours. In this method, a liposome composition of the type described above is administered intravenously to a subject at a dose which contains an amount of the compound which is at least three times such therapeutically effective amount Also disclosed is a liposome composition effective to extend to at least one week, the period of effective activity of an therapeutic compound which can be administered intravenously in a therapeutically effective amount. The composition includes liposomes (i) composed of vesicle-forming lipids and between 1-20 mole percent of a vesicle-forming lipid derivatized with a biocompatible hydrophilic polymer, and (ii) having a selected mean particle diameter in the size range between about 0.07–0.15 microns, and the compound in liposome-entrapped form. The composition is intended for subcutaneous administration at a dose which contains an amount of the liposome-entrapped compound which is at least ten times such therapeutically effective intravenously administered amount.

The liposome composition is used in a method for extending the period of release of a therapeutic compound, preferably a polypeptide, in a therapeutically active amount, for a period of at least 2 weeks.

In another aspect, the invention includes a liposome composition composed of vesicle-forming lipids and a vesicle-forming lipid derivatized with polylactic acid or polyglycolic acid, and a lipid composition composed of a vesicle-forming lipid having a polar head group, and a polylactic acid or polyglycolic acid moiety derivatized to the lipid's head group.

These and other objects and features of the present invention will become more fully apparent when the following detailed description of the invention is read in conjunction with the accompanying drawings.

DETAILED DESCRIPTION OF THE INVENTION

I. Preparation of Derivatized Lipids

Figure 1:
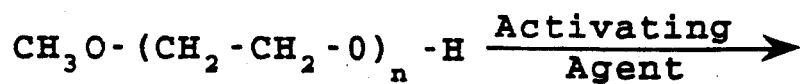
FIG. 1 illustrates a general reaction scheme for derivatizing a vesicle-forming lipid amine with a polyalkyl-ether.
Figure 1:
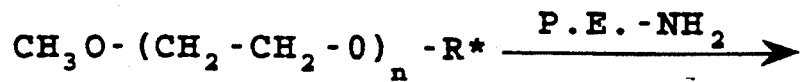
Figure 1:
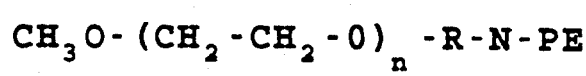

FIG. 1 shows a general reaction scheme for preparing a vesicle-forming lipid derivatized with a biocompatible, hydrophilic polymer, as exemplified by polyethylene glycol (PEG), polylactic acid, and polyglycolic acid, all of which are readily water soluble, can be coupled to vesicle-forming lipids, and are tolerated in vivo without toxic effects. The hydrophilic polymer which is employed, e.g., PEG, is preferably capped by a methoxy, ethoxy or other unreactive group at one end, or is one in which one end is more reactive than the other, such as polylactic acid.

The polymer is activated at one end by reaction with a suitable activating agent, such as cyanuric acid, diimadozle, anhydride reagent, or the like, as described below. The activated compound is then reacted with a vesicle-forming lipid, such as phosphatidylethanol (PE), to produce the derivatized lipid.

Alternatively, the polar group in the vesicle-forming lipid may be activated for reaction with the polymer, or the two groups may be joined in a concerted coupling reaction, according to known coupling methods. PEG capped at one end with a methoxy or ethoxy group can be obtained commercially in a variety of polymer sizes, e.g., 500-20,000 dalton molecular weights.

The vesicle-forming lipid is preferably one having two hydrocarbon chains, typically acyl chains, and a polar head group. Included in this class are the phospholipids, such as phosphatidylcholine (PC), PE, phosphatidic acid (PA), phosphatidylinositol (PI), and sphingolipids such as sphingomyelin (SM), where the two hydrocarbon chains are typically between about 14-22 carbon atoms in length, and have varying degrees of unsaturation. Also included in this class are the glycolipids, such as cerebrosides and gangliosides.

Another vesicle-forming lipid which may be employed is cholesterol and related sterols In general, cholesterol may be less tightly anchored to a lipid bilayer membrane, particularly when derivatized with a high molecular weight polyalkylether, and therefore be less effective in promoting liposome evasion of the RES in the bloodstream.

More generally, and as defined herein, "vesicle-forming lipi" is inene to include any amphipathic lipid having hydrophobic and polar head group moieties, and which (a) by itself can form spontaneously into bilayer vesicles in water, as exemplified by phospholipids, or (b) is stably incorporated into lipid bilayers in combination with phospholipids, with its hydrophobic moiety in contact with the interior, hydrophobic region of the bilayer membrane, and its polar head group moiety oreinted toward the exterior, polar surface of the membrane. An example of a latter type of vesicle-forming lipid is cholesterol and cholesterol derivatives, such as cholesterol sulfate and cholesterol hemisuccinate.

According to one important feature of the invention, the vesicle-forming lipid may be a relatively fluid lipid, meaning that the lipid phase has a relatively low liquid-to-liquid crystal phase-transition temperature, e.g., at or below room temperature, or relatively rigid lipid, meaning that the lipid has a relatively high melting temperature, e.g., up to 50° C. As a rule, the more rigid, i.e., saturated lipids, contribute to greater membrane rigidity in a lipid bilayer structure and also contribute to greater bilayer stability in serum. Other lipid components, such as cholesterol, are also known to contribute to membrane rigidity and stability in lipid bilayer structures. Phospholipids whose acyl chains have a variety of degrees of saturation can be obtained commercially, or prepared according to published methods.

Figure 2:
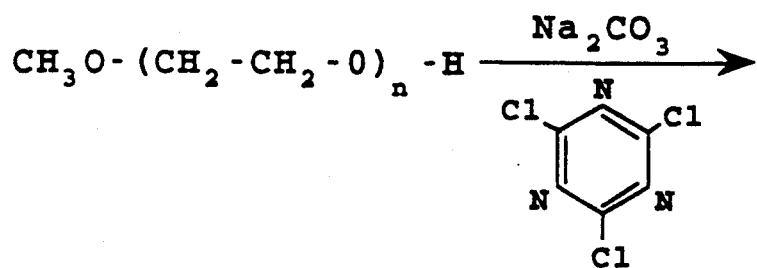
FIG. 2 is a reaction scheme for preparing phosphatidylethanolamine (PE) derivatized with polyethyleneglycol via a cyanuric chloride linking agent.
Figure 2:
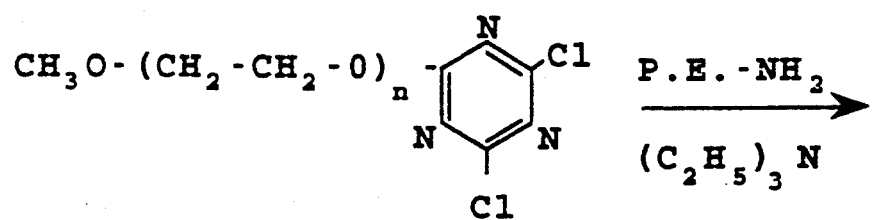
Figure 2:
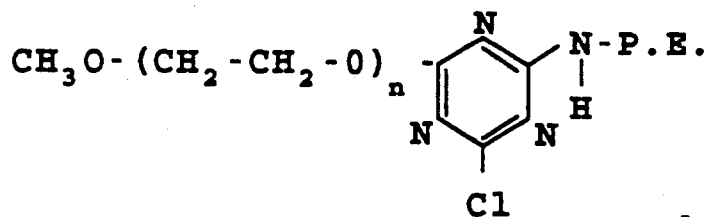

FIG. 2 shows a reaction scheme for producing a PE-PEG lipid in which the PEG is derivatized to PE through a cyanuric chloride group. Details of the reaction are provided in Example 1. Briefly, methoxy-capped PEG is activated with cyanuric chloride in the presence in sodium carbonate under conditions which produced the activated PEG compound in the figure. This material is purified to remove unreacted cyanuric acid. The activated PEG compound is reacted with PE in the presence of triethyl amine to produce the desired PE-PEG compound, also shown in the figure. The yield is about 8-10% with respect to initial quantities of PEG.

The method just described may be applied to a variety of lipid amines, including PE, cholesteryl amine, and glycolipids with sugar-amine groups.

Figure 3:
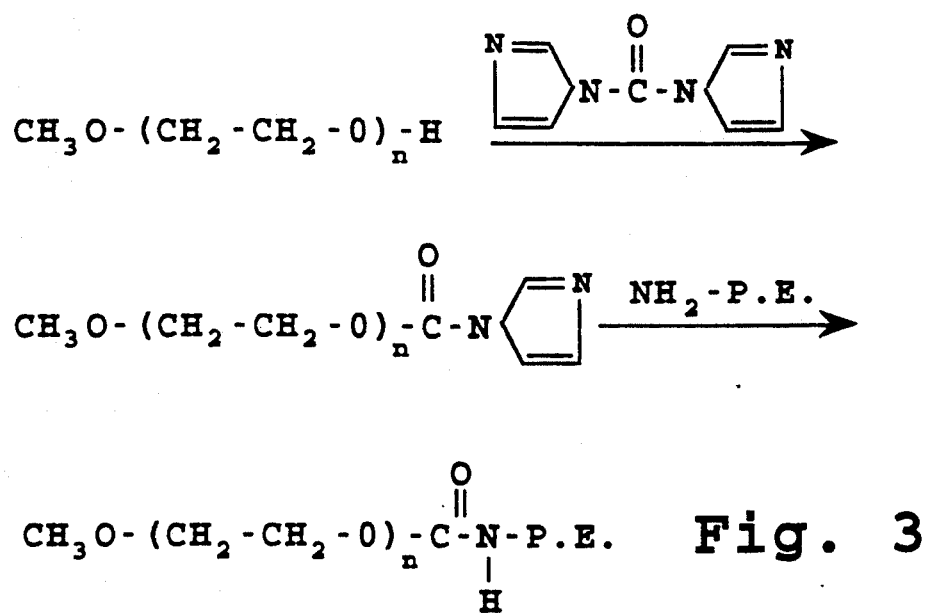
FIG. 3 illustrates a reaction scheme for preparing phosphatidylethanolamine (PE) derivatized with polyethyleneglycol by means of a diimidazole activating reagent.

A second method of coupling a polyalkylether, such as capped PEG to a lipid amine is illustrated in FIG. 3. Here the capped PEG is activated with a carbonyl diimidazole coupling reagent, to form the activated imidazole compound shown in FIG. 3. Reaction with a lipid amine, such as PE leads to PEG coupling to the lipid through an amide linkage, as illustrated in the PEG-PE compound shown in the figure Details of the reaction are given in Example 2.

Figure 4:
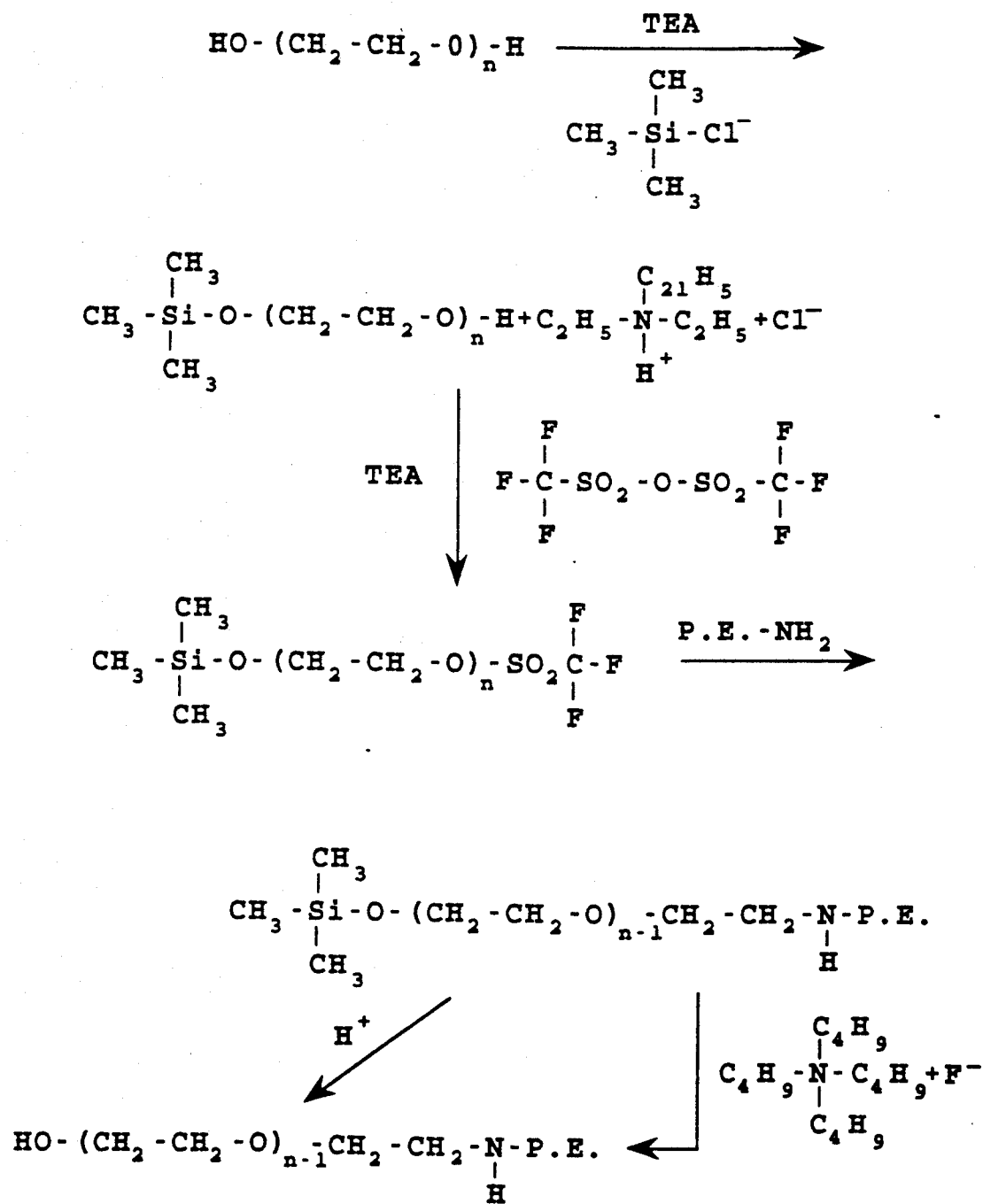
FIG. 4 illustrates a reaction scheme for preparing phosphatidylethanolamine (PE) derivatized with polyethyleneglycol by means of a trifluoromethane sulfonate reagent.

A third reaction method for coupling a capped polyalkylether to a lipid amine is shown in FIG. 4. Here PEG is first protected at its OH end by a trimethylsilane group. The end-protection reaction is shown in the figure, and involves the reaction of trimethylsilylchloride with PEG in the presence of triethylamine. The protected PEG is then reacted with the anhydride of trifluoromethyl sulfonate (FIG. 4) to form the PEG compound activated with trifluoromethyl sulfonate. Reaction of the activated compound with a lipid amine, such as PE, in the presence of triethylamine, gives the desired derivatized lipid product, such as the PEG-PE compound, in which the lipid amine group is coupled to the polyether through the terminal methylene carbon in the polyether polymer. The trimethylsilyl protective group can be released by acid treatment, as indicated at H+ in the figure, or by reaction with a quaternary amine fluoride salt, such as the fluoride salt of tetrabutylamine.

It will be appreciated that a variety of known coupling reactions, in addition to those just described, are suitable for preparing vesicle-forming lipids derivatized with hydrophilic polymers such as PEG, polylactic acid, or polyglycolic acid. For example, the sulfonate anhydride coupling reagent illustrated in FIG. 4 can be used to join an activated polyalkylether to the hydroxyl group of an amphipathic lipid, such as the 5'-OH of cholesterol. Other reactive lipid groups, such as an acid or ester lipid group may also be used for coupling, according to known coupling methods. For example, the acid group of phosphatidic acid can be activated to form an active lipid anhydride, by reaction with a suitable anhydride, such as acetic anhydride, and the reactive lipid can then be joined to a protected polyalkylamine by reaction in the presence of an isothiocyanate reagent.

Figure 5A:
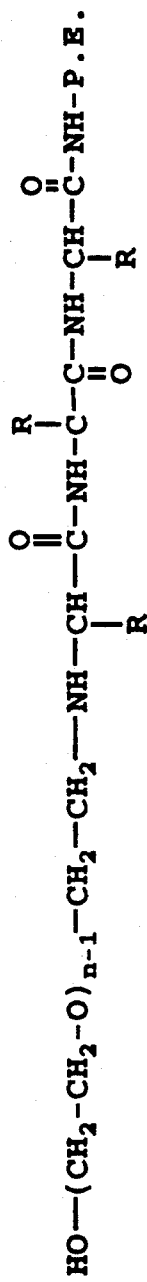
FIGS. 5A, 5B and 5C illustrate a vesicle-forming lipid derivatized with polyethylene glycol through a peptide, ester and disulfide linkage respectively.
Figure 5B:
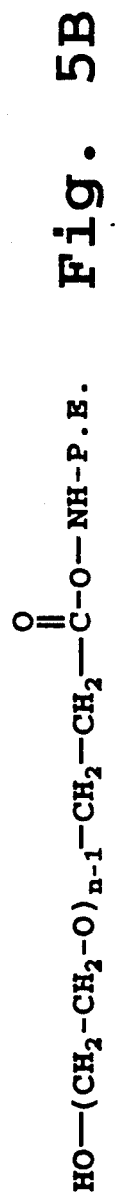
Figure 5C:
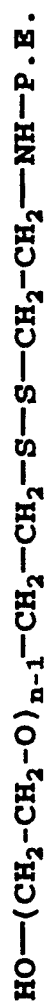

In another embodiment, the derivatized lipid components are prepared to include a labile lipid-polymer linkage, such as a peptide, ester, or disulfide linkage, which can be cleaved under selective physiological conditions, such as in the presence of peptidase or esterase enzymes or reducing agents such as glutathione present in the bloodstream. FIG. 5 shows exemplary lipids which are linked through (A) peptide, (B) ester, and (C), disulfide containing linkages. The peptide-linked compound can be prepared, for example, by first coupling a polyalkylether with the N-terminal amine of the tripeptide shown, e.g., via the reaction shown in FIG. 3. The peptide carboxyl group can then be coupled to a lipid amine group through a carbodiimide coupling reagent conventionally. The ester linked compound can be prepared, for example, by coupling a lipid acid, such as phosphatidic acid, to the terminal alcohol group of a polyalkylether, using alcohol via an anhydride coupling agent. Alternatively, an short linkage fragment containing an internal ester bond and suitable end groups, such as primary amine groups can be used to couple the polyalkylether to the amphipathic lipid through amide or carbamate linkages. Similarly, the linkage fragment may contain an internal disulfide linkage, for use in forming the compound shown at C in FIG. 5.

Figure 6:
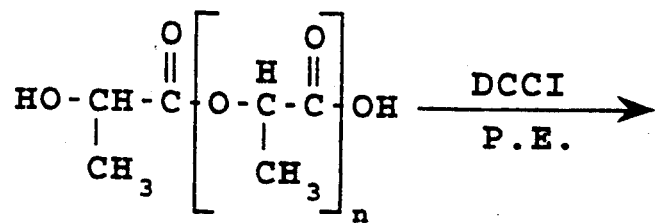
FIG. 6 illustrates a reaction scheme for preparing phosphatidylethanolamine (PE) derivatized with polylactic acid.
Figure 6:
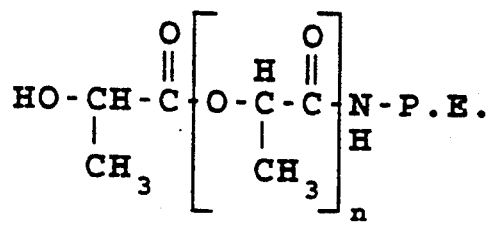

FIG. 6 illustrates a method for derivatizing polylactic acid with PE. The polylactic acid is reacted, in the presence of PE, with dicyclohexylcarboimide (DCCI), as detailed in Example 2. Similarly, a vesicle-forming lipid derivatized with polyglycolic acid may be formed by reaction of polyglycolic acid or glycolic acid with PE in the presence of a suitable coupling agent, such as DCCI, also as detailed in Example 2. The vesicle-forming lipids derivatized with either polylactic acid or polyglycolic acid form part of the invention herein. Also forming part of the invention are liposomes containing these derivatized lipids, in a 1-20 mole percent.

II. Preparation of Liposome Composition

A. Lipid Components

The lipid components used in forming the liposomes of the invention may be selected from a variety of vesicle-forming lipids, typically including phospholipids and sterols. As will be seen, one requirement of the liposomes of the present invention is long blood circulation lifetime. It is therefore useful to establish a standardized measure of blood lifetime which can be used for evaluating the effect of lipid components on blood halflife.

One method used for evaluating liposome circulation time in vivo measures the distribution of IV injected liposomes in the bloodstream and the primary organs of the RES at selected times after injection. In the standardized model which is used herein, RES uptake is measured by the ratio of total liposomes in the bloodstream to total liposomes in the liver and spleen, the principal organs of the RES. In practice, age and sex matched mice are injected intravenously (IV) through the tail vein with a radiolabeled liposome composition, and each time point is determined by measuring total blood and combined liver and spleen radiolabel counts, as detailed in Example 6.

Since the liver and spleen account for nearly 100% of the initial uptake of liposomes by the RES, the blood/RES ratio just described provides a good approximation of the extent of uptake from the blood to the RES in vivo. For example, a ratio of about 1 or greater indicates a predominance of injected liposomes remaining in the bloodstream, and a ratio below about 1, a predominance of liposomes in the RES. For most of the lipid compositions of interest, blood/RES ratios were calculated at 1, 2, 3, 4, and 24 hours.

The liposomes of the present invention include 1-20 mole percent of the vesicle-forming lipid derivatized with a hydrophilic polymer, described in Section I. According to one aspect of the invention, it has been discovered that blood circulation halflives in these liposomes are largely independent of the degree of saturation of the phospholipid components making up the liposomes. That is, the phospholipid components may be composed of predominantly of fluidic, relatively unsaturated, acyl chains, or of more saturated, rigidifying acyl chain components. This feature of the invention is seen in Example 7, which examines blood/RES ratios in liposomes formed with PEG-PE, cholesterol, and PC having varying degrees of saturation (Table 4). As seen from the data in Table 5 in the example, high blood/RES ratios were achieved with in substantially all of the liposome formulations, independent of the extent of lipid unsaturation in the bulk PC phospholipid, and no systematic trend, as a function of degree of lipid saturation, was observed.

Accordingly, the vesicle-forming lipids may be selected to achieve a selected degree of fluidity or rigidity, to control the stability of the liposomes in serum and the rate of release of entrapped drug from the liposomes in the bloodstream and/or tumor. The vesicle-forming lipids may also be selected, in lipid saturation characteristics, to achieve desired liposome preparation properties. It is generally the case, for example, that more fluidic lipids are easier to formulate and down size by extrusion or homogenization than more rigid lipid components. In general, more fluidic lipids (low transition temperature) are preferred because of high compound-release rates in the bloodstream.

Similarly, it has been found that the percentage of cholesterol in the liposomes may be varied over a wide range without significant effect on observed blood/RES ratios The studies presented in Example 8A, with reference to Table 6 therein, show virtually no change in blood/RES ratios in the range of cholesterol between 0-30 mole percent.

Cholesterol, or related cholesterol derivatives may be important, however, in regulating the rate of release of liposome entrapped therapeutic compounds into the bloodstream. The studies reported in Examples 15 and 16, for example, indicate that the rate of release of encapsulated polypeptide (peptide or protein) from liposomes in vitro (in the presence of human serum) or in vivo (in the bloodstream) is strongly dependent on cholesterol concentration PEG-liposome formulations containing high cholesterol (e.g., 30 mole percent or greater) release very little peptide or protein into serum in vitro, whereas decreasing amounts of cholesterol produce increasing loss of encapsulated polypeptide Similarly, and as described below, increased cholesterol in intravenously administered PEG-liposomes produced reduced release of encapsulated compound into the bloodstream (Example 16) and reduced physiological effect (Example 15). Thus, in accordance with one feature of the invention, the rate of release of compound from long-circulating liposomes can be controlled by the percent cholesterol included in the liposomes.

It has also been found, in studies conducted in support of the invention, that blood/RES ratios are also relatively unaffected by the presence of charged lipid components, such as phosphatidylglycerol (PG). This can be seen from FIG. 7, which plots percent loss of encapsulated marker for PEG-PE liposomes containing either 4.7 mole percent PG (triangles) or 14 mole percent PG (circles). Virtually no difference in liposome retention in the bloodstream over a 24 hour period was observed In one embodiment, the liposomes are formulated to contain diglyceride at a mole ratio of up to 25 mole percent or more total liposome lipids Such liposomes are characterized by rapid liposome breakdown in the bloodstream, with release of encapsulated material, and the rate of breakdown can be selectively controlled by the percent of diglyceride included in the liposomes. The ability of the such liposomes to avoid uptake by the RES, and at the same time, to break down in the bloodstream over a period of 2-12 hours or more in the bloodstream provides a composition for achieving delayed release of an intravenously administered drug over a several hour period, and which also avoids drug accumulation predominantly in the RES tissues The vesicle-forming lipid derivatized with a hydrophilic polymer is present in an amount preferably between about 1-20 mole percent, on the basis of moles of derivatized lipid as a percentage of total moles of vesicle-forming lipids. It will be appreciated that a lower mole ratio, such as 0.1 mole percent, may be appropriate for a lipid derivatized with a large molecular weight polymer, such as one having a molecular weight greater than 100 kilodaltons. As noted in Section I, the hydrophilic polymer in the derivatized lipid preferably has a molecular weight between about 200-20,000 daltons, and more preferably between about 1,000-5,000 daltons. Example 8B, which examines the effect of very short ethoxy ether moieties on blood/RES ratios indicates that polyether moieties of greater than about 5 carbon ether are required to achieve significant enhancement of blood/RES ratios.

B. Preparing the Liposome Composition

The liposomes may be prepared by a variety of techniques, such as those detailed in Szoka et al, 1980. One method for preparing drug-containing liposomes is the reverse phase evaporation method described by Szoka et al and in U.S. Pat. No. 4,235,871. The reverse phase evaporation vesicles (REVs) have typical average sizes between about 2-4 microns and are predominantly oligolamellar, that is, contain one or a few lipid bilayer shells. The method is detailed in Example 5A. This method is generally preferred for preparing liposomes with encapsulated proteins high encapsulation efficiencies (up to 50%) are possible, and thus protein loss or problems of recovery and purification of non-encapsulated protein are reduced.

Multilamellar vesicles (MLVs) can be formed by simple lipid-film hydration techniques. In this procedure, a mixture of liposome-forming lipids of the type detailed above dissolved in a suitable solvent is evaporated in a vessel to form a thin film, which is then covered by an aqueous medium, as detailed in Example 5B. The lipid film hydrates to form MLVs, typically with sizes between about 0.1 to 10 microns.

In accordance with one important aspect of the invention, the liposomes for intravenous injection are prepared to have substantially homogeneous sizes in a selected size range between about 0.1 and 0.4, and preferably 0.1 to 0.2 micron size ranges. Liposomes in this size range have sufficiently high encapsulation volumes for carrying therapeutically effective amounts of the compound to be administered. At lower liposome sizes, the ratio of liposome-encapsulated compound to free compound may be too low to achieve a requisite initial dose level of liposome-encapsulated compound in the bloodstream or may not remain in circulation due to extravasation. At the same time, 0.1-0.4 micron liposomes are small enough to give long blood circulation times, as discussed below, and also to allow sterilization by filtration.

One effective sizing method for REVs and MLVs involves extruding an aqueous suspension of the liposomes through a polycarbonate membrane having a selected uniform pore size, typically 0.4, 0.2, and/or 0.1 micron pore sizes. The pore size of the membrane is related to the largest sizes of the liposomes which are produced, particularly where the preparation is extruded two or more times through the same size membrane. This method of liposome sizing is used in preparing homogeneous-size REV and MLV compositions described in the examples below. A more recent method involves extrusion through an asymmetric ceramic filter. The method is detailed in U.S. Pat. No. 4,737,323 for Liposome Extrusion Method. Homogenization methods are also useful for down-sizing liposomes.

Figure 19A:
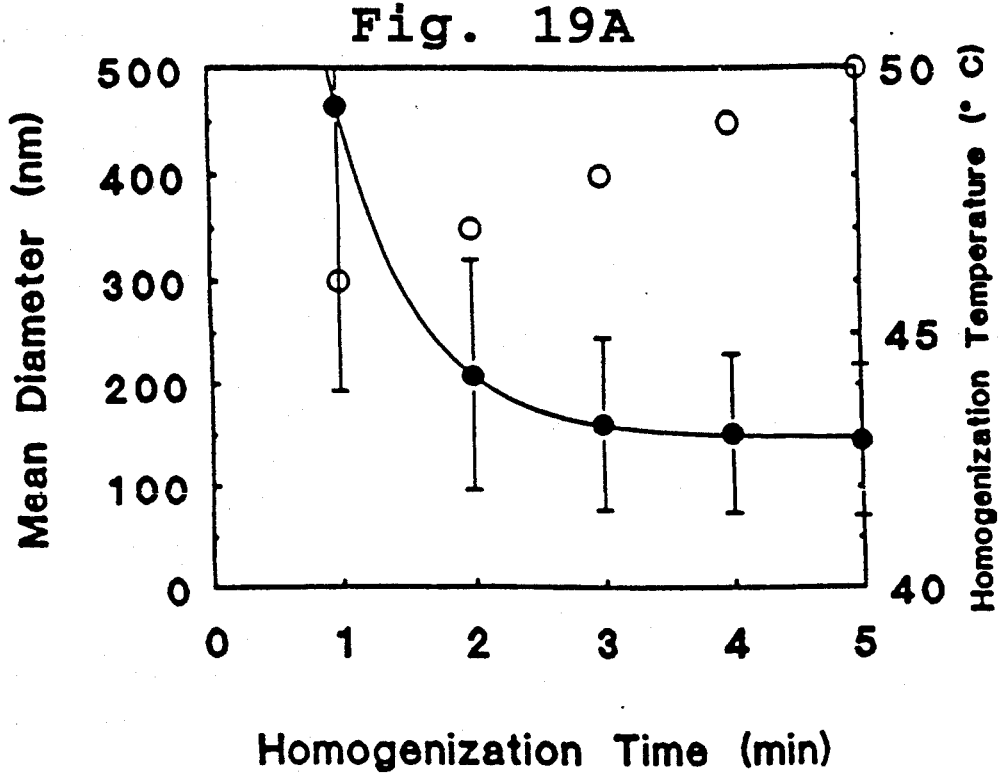
FIGS. 19A and 19B show the change in PEG-liposome size, as a function of homogenization time, for liposome particles in an homogenized suspension.
Figure 19B:
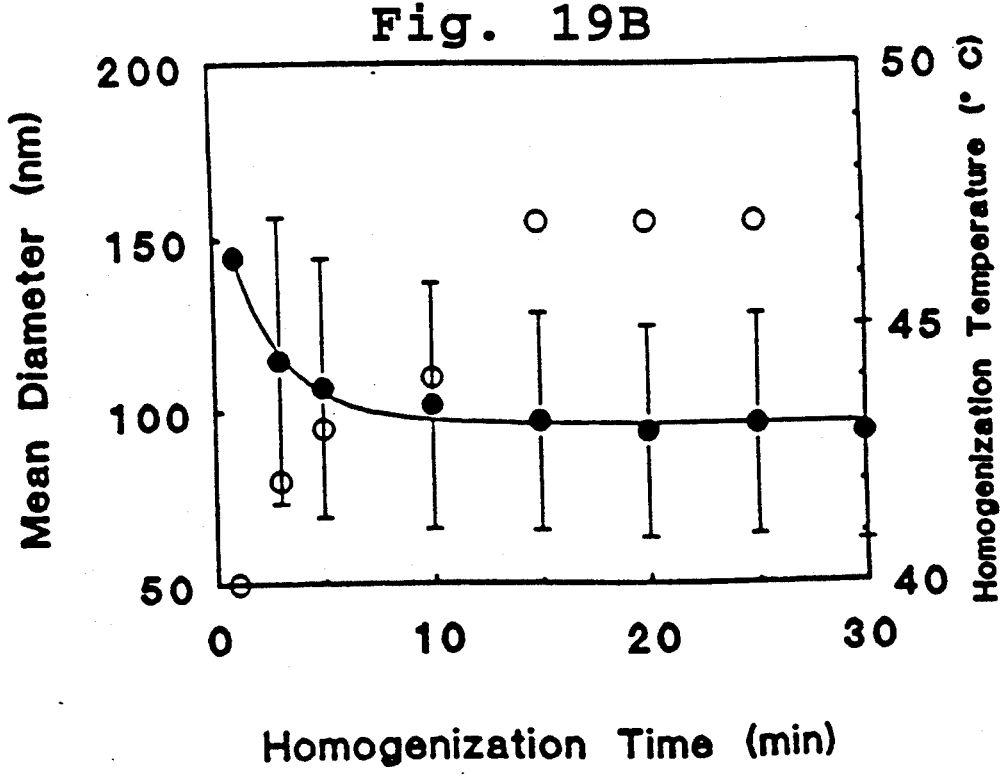

It has also been discovered, in liposome processing studies carried out in support of the present invention, that liposomes coated with a hydrophilic polymer, such as PEG, can be formed with mean particle sizes of about 100-200 nm or less by homogenization at less than 8,000 psi and at a temperature less than 50° C. This is in contrast to conventional liposomes, for which homogenization pressures of between 8,000-13,000 psi, and temperatures between about 50°-80° C. are required to produce particles in this size range (e.g., as reported in U.S. Pat. No. 4,753,788). In one method, reported in Example 5E, sized liposomes were prepared by homogenization at 8,000 psi at 50° C. at homogenization times up to 30 minutes, where the material was cycled at a rate of about once per minute. Mean particle size, as a function of homogenization time, is shown in FIGS. 19A and 19B. As seen, particles sizes in the desired size range (about 100 nm) were produced after 3–5 homogenization cycles.

The liposome composition of the invention may also be prepared by diffusing a lipid derivatized with a hydrophilic polymer, such as PEG-PC, into preformed liposomes. In a typical method, liposomes prepared in the absence of polymer-derivatized lipid are incubated with micelles of the derivatized lipid, at a lipid concentration corresponding to the final mole percent of derivatized lipid which is desired. Thus, for example, to form PEG-liposomes containing 10 mole percent PEG, liposomes may be incubated with 10 mole percent PEG-PV micelles. Incubation is carried out with stirring until substantially all of the derivatized lipid has diffused into the liposomes. Typical incubation times are 2 hours at 60° C., or 24 hours at 37° C.

The just-described method is useful, for example, when the liposomes are prepared to include covalently attached ligand surface molecules, such as antigen or antibody molecules, for liposome targeting or to achieve some other ligand-specific liposome interaction. Here, the liposomes are first reacted with the ligand, for covalent attachment to the liposome surface, according to conventional liposome coupling methods, and the ligand-coated liposomes are then mixed with the derivatized lipid, for anchoring hydrophilic polymer to the liposome surface.

C. Compound Loading

In one embodiment, the composition of the invention is used for slow-release delivery into the bloodstream of a polypeptide (peptide or protein) which is therapeutically active in the bloodstream when administered IV, but which in free form has a short blood halflife, typically 4 hours or less. Examples of such polypeptides include hormones, such as vasopressin, calcitonin, oxytocin, somatotropin, human growth hormone, atrial naturectic factor (ANF), and insulin; enzymes, such as superoxide dismutase, glucocerebrosidase, asparaginase, and adenosine deaminase; immunomodulators, such as interferons (alpha, beta, and gamma)., interleukin (1,2,3,4,5,6,7), tissue necrosis factor (TNF-alpha, beta), and colony stimulating factors (M-CSF (macrophage), G-CSF (granulocyte), GM-CSF (granulocyte, macrophage); anticoagulants, such as TPA, prourokinase, and urokinase; vaccines, such as HIV-1 vaccine, hepatitis B vaccine, malaria vaccine, and melanoma vaccine; and other polypeptides (peptides and proteins), such as erythropoietin (EPO), factor VIII, bone growth factor, fibroblast growth factor, insulin-like growth factor, nerve growth factor, platelet-derived growth factor, tumor growth factors (alpha, beta), and somatomedin C (IGF-1); and ribosome-inhibitor proteins, such as pokeweed antiviral protein peptide receptor antagonists such as those which inhibit binding of IL-1 and TNF and gelonin.

The polypeptides useful in the invention typically have relatively short blood halflives, on the order of 2–4 hours or less, and are active in the picogram/ml to nanogram/ml concentration range in the blood.

As noted above, a polypeptide is preferably loaded passively by the reverse-phase emulsion method for preparing liposomes, although many other methods, such as solvent injection or lipid hydration may be employed. After liposome formation and sizing, free (unbound) drug can be removed by a variety of methods, for example, by gel filtration or ion exchange chromatography or diafiltration. Typically the amount of free peptide in the final sterilized composition is less than about 20%, and preferably less than 10% of the total polypeptide contained in the composition.

At the same time, the encapsulated compound is preferably present in an amount which, in a selected liposome dose, is between 3–20 times the amount of compound which would be given as a single therapeutic dose in free form by IV administration. Thus, if the therapeutic dose of a peptide in free form is 1 $\mu$g for IV administration, a selected liposome dose will preferably contain between about 3–20 $\mu$g of the peptide. Since 10–20% of this compound, e.g., 2–4 $\mu$g, may be in non-encapsulated form, it will be appreciated that the total amount of liposome which can be administered may be limited by the maximum tolerated dose of the free compound It is clear that larger doses of liposomes can be administered by achieving higher ratios of encapsulated to non-encapsulated compound. In general, this ratio is increased with larger liposomes, more complete free drug removal from the liposome composition, and greater liposome stability on storage.

The composition is also useful for slow-release delivery of a variety of non-peptide, water-soluble compounds which are effective in treating circulating cancers such as leukemias, which are sensitive to cell-cycle-specific anti-tumor drugs, for example, cytarabine, cyclophosphamide, carmustine, thioguanine, bleomycin, daunorubicin, vinblastine, vincristine, and asparaginase.

Also useful in therapeutic delivery by the present invention are antibiotics, such as gentamicin, tobramycin, amikacin, netilmicin, kanamycin, and streptomycin, cefotaxime, ceftizoxime, and ceftriaxone, and anti-viral agents, such as AZT (zidovidine), DDI (dideoxyinosine), DDC (didioxycytidine), ganciclovir, D4T (didihydrodeoxythymidine), phosphonoformate, ribavirin, and acyclovir.

Such compounds may be encapsulated by passive loading, as above, during liposome formation by reverse evaporation phase, lipid hydration, solvent injection, or other liposome formation methods, and removed, after sizing by gel filtration or the like.

Alternatively, drugs which form weak bases at physiological pH may be actively loaded into the liposomes at high drug concentration in the liposomes. One method for active loading drugs into liposomes is described in co-owned U.S. patent application Ser. No. 413,037, filed Sep. 28, 1988. In this method, liposomes are prepared in the presence of a relatively high ammonium ion, such as 0.125M ammonium sulfate. After sizing the liposomes to a desired size, the liposome suspension is treated to create an inside-to-outside ammonium ion gradient across the liposomal membranes. The gradient may be created by dialysis against a non-ammonium containing medium, such as an isotonic glucose medium, or by gel filtration, such as on a Sephadex G-50 column equilibrated with 0.15M NaCl or KCl, effectively replacing ammonium ions in the exterior phase with sodium or potassium ions. Alternatively, the liposome suspension may be diluted with a non-ammonium solution, thereby reducing the exterior-phase concentration of ammonium ions. The ammonium concentration inside the liposomes is preferably at least 10 times, and more preferably at least 100 to 1000 times that in the external liposome phase.

The ammonium ion gradient across the liposomes in turn creates a pH gradient, as ammonia is released across the liposome membrane, and protons are trapped in the internal liposome phase. To load liposomes with the selected drug, a relatively dilute suspension of the liposomes, e.g., less than about 50 mM lipid, is mixed with an aqueous solution of the drug, and the mixture is allowed to equilibrate over a period of time, e.g., 24 hours at room temperature. In one typical method, a suspension of liposomes having a lipid concentration of 25 mg/ml is mixed with an equal volume of anthracycline drug at a concentration of about 10 mg/ml. At the end of the incubation period, the suspension is treated to remove free (unbound) drug.

III. Intravenous Administration

A. Extended Lifetime in the Bloodstream

One of the requirements for extended compound release into the bloodstream, in accordance with the invention, is an extended liposome lifetime in the bloodstream with IV liposome administration. One measure of liposome lifetime in the bloodstream in the blood/RES ratio determined at a selected time after liposome administration, as discussed above. Blood/RES ratios for a variety of liposome compositions are given in Table 3 of Example 6. In the absence of PEG-derivatized lipids, blood/RES ratios were 0.03 or less. In the presence of PEG-derivatized lipids, the blood/RES ratio ranged from 0.2, for low-molecular weight PEG, to between 1.7-4 for several of the formulations, one of which lacks cholesterol, and three of which lack a charged phospholipid (e.g., PG).

The data presented in Table 5 in Example 7 show blood/RES ratios (excluding the two points with low percent recovery which are considered unreliable) between about 1.26 and 3.27, consistent with the data given in Table 3. As noted in Section II above, the blood lifetime values are substantially independent of degree of saturation of the liposome lipids, presence of cholesterol, and presence of charged lipids.

The blood/RES values reported above can be compared with blood/RES values reported in co-owned U.S. Pat. No. 4,920,016, which used blood/RES measurement methods similar to those used in for the data presented in Tables 3 and 5. The best 24-hour blood/RES ratios which were reported in the above-noted patent was 0.9, for a formulation composed of $GM_1$, saturated PC, and cholesterol. The next best formulations gave 24-hour blood/RES values of about 0.5. Thus, typical 24-hour blood/RES ratios obtained in a number of the current formulations were more than twice as high as the best formulations reported which have been reported to date. Further, and unlike the present invention, ability to achieve high blood/RES with $GM_1$ or HPI lipids was dependent on the presence of predominantly saturated lipids in the liposomes.

Figure 7:
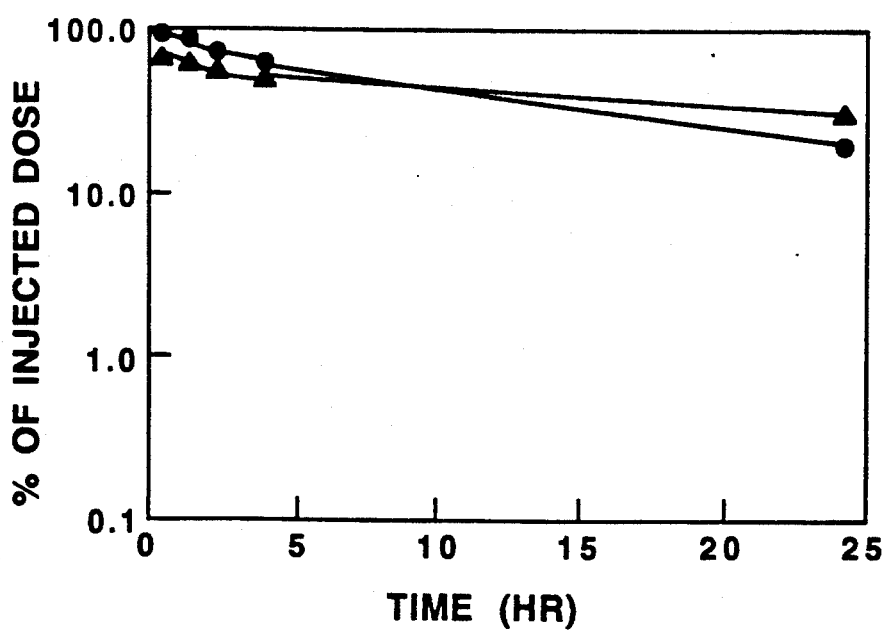
FIG. 7 is a plot of liposome retention time in the blood, expressed in terms of percent injected dose as a function of hours after IV injection, for PEG-PE liposomes containing different amounts of phosphatidylglycerol.
Figure 8:
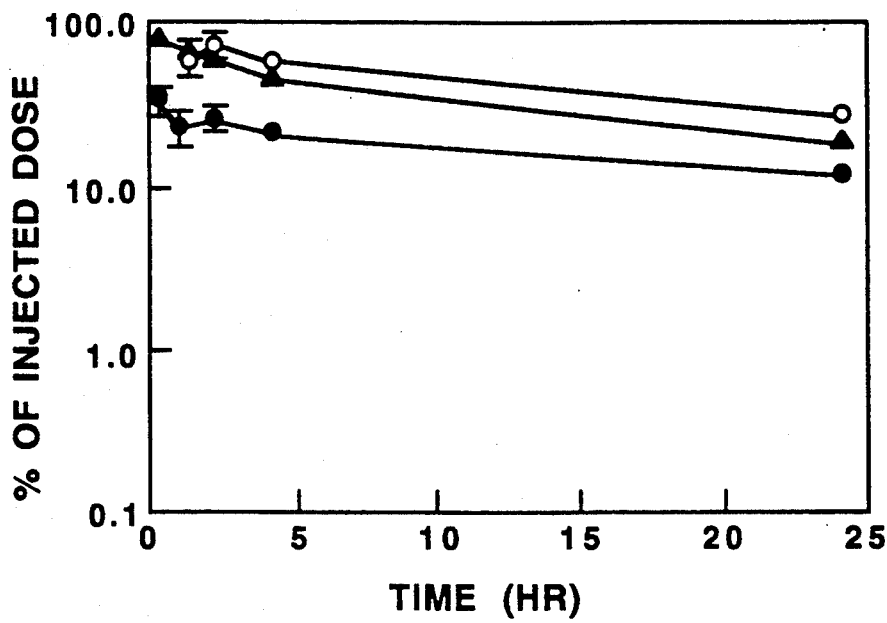
FIG. 8 is a plot similar to that of FIG. 7, showing retention times in the blood of liposomes composed of predominantly unsaturated phospholipid components.

Plasma kinetics of a liposomal marker in the bloodstream can provide another measure of the enhanced liposome lifetime which is achieved by the liposome formulations of the present invention. FIGS. 7 and 8 discussed above show the slow loss of liposomal marker over a 24 hour period in typical PEG-liposome formulations, substantially independent of whether the marker is a lipid or an encapsulated water-soluble compound (FIG. 8). In both plots, the amount of liposomal marker present 24 hours after liposome injection is greater than 10% of the originally injected material.

Figure 9:
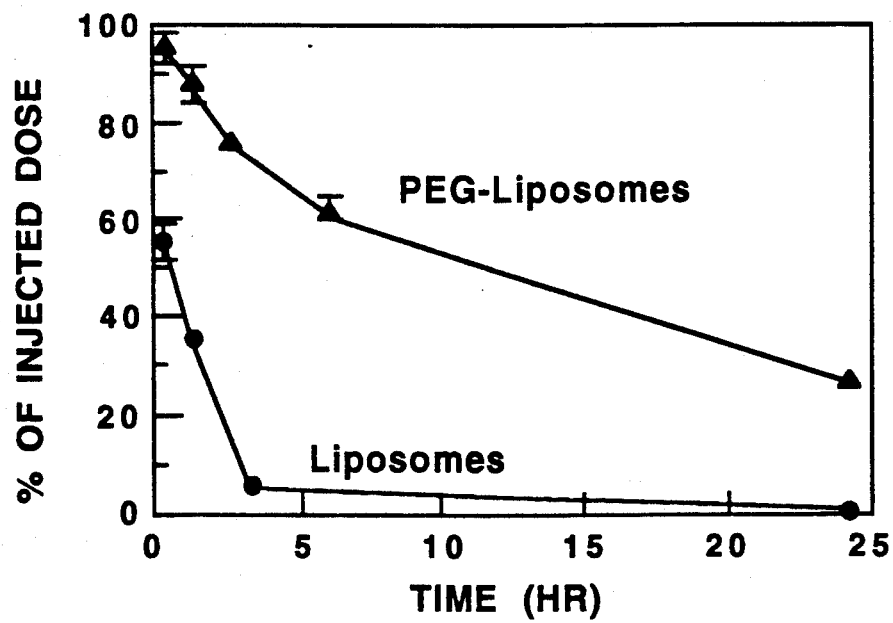
FIG. 9 is a plot similar to that of FIG. 7, showing retention times in the blood of PEG liposomes (solid triangles) and conventional liposomes (solid circles)

FIG. 9 shows the kinetics of liposome loss from the bloodstream for a typical PEG-liposome formulation and the same liposomes in the absence of a PEG-derivatized lipid. After 24 hours, the percent marker remaining in the PEG-liposomes was greater than about 20%, whereas the conventional liposomes showed less than 5% retention in the blood after 3 hours, and virtually no detectable marker at 24 hours.

The results seen in FIGS. 7-9 are consistent with 24 hour blood liposome values measured for a variety of liposome formulations, and reported in Tables 3 and 5-7 in Example 6-9 below. As seen Table 3 in Example 6, the percent dose remaining at 24 hours was less than 1% for conventional liposomes, versus at least 5% for the PEG-liposomes. In the best formulations, values between about 20-40% were obtained. Similarly in Table 5 from Example 7, liposome levels in the blood after 24 hours (again neglecting two low recovery values) were between 12 and about 25 percent of total dose given. Similar results are reported in Tables 6 and 7 of Example 8.

Figure 10:
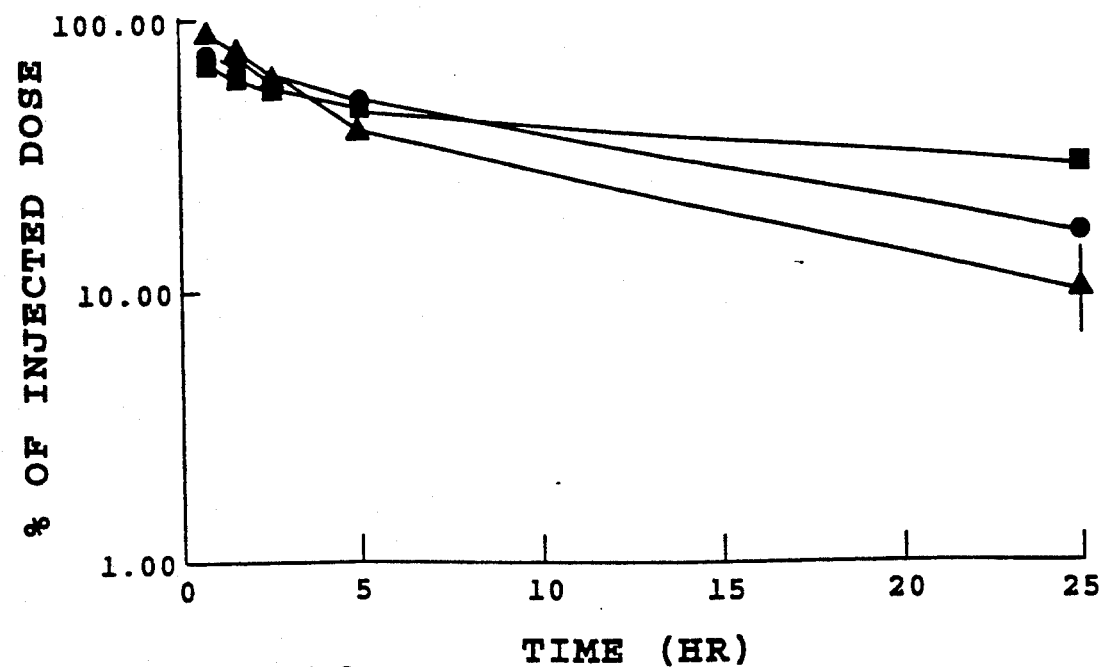
FIG. 10 is a plot of blood lifetimes of PEG-liposomes sized by extrusion through 0.1 micron (solid squares), 0.2 micron (solid circles), and 0.4 micron (solid triangles) polycarbonate membranes.

The effect of liposome size on blood lifetime was been investigated by comparing loss of liposomal marker in intravenously injected liposomes having selected sizes between about 0.1 and 0.25 microns. Experimental details are given in Example 10. The results, given in FIG. 10, show about 10% or greater liposome marker present in the blood after 24 hours for each of the liposome formulations. Highest blood lifetimes were achieved with the smallest liposomes. Thus, although all of the liposome preparations give high blood lifetimes, it is also clear that liposome size can be selected to produce desired increase or decrease in total drug release time.

Figure 11:
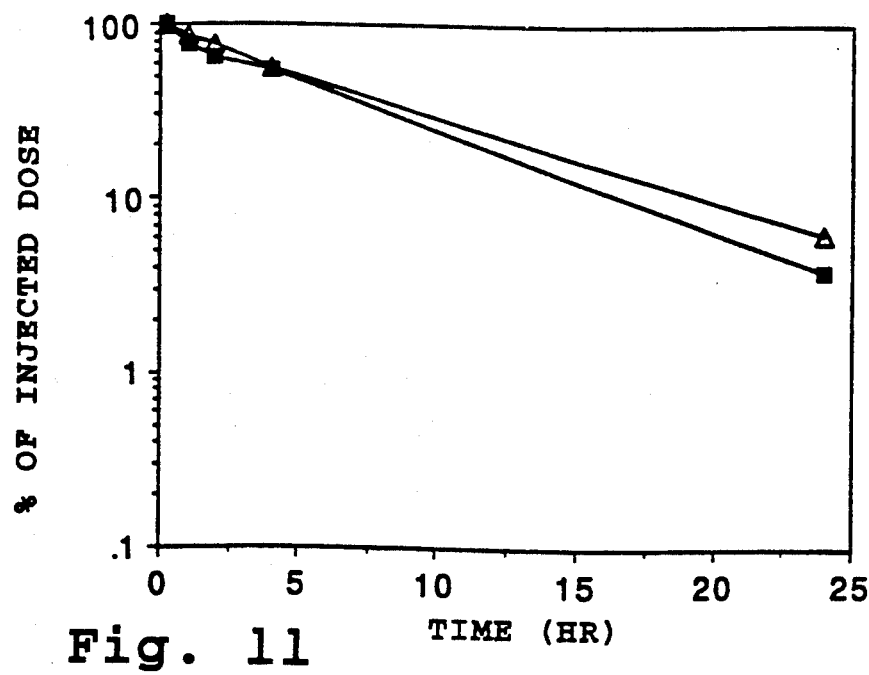
FIG. 11 is a plot of blood retention times in liposomes containing a vesicle-forming lipid derivatized with polylactic acid (solid squares) and polyglycolic acid (open triangles)

The enhancement in liposome blood circulation time achieved with two other biocompatible hydrophilic polymers, polylactic acid and polyglycolic acid, is seen in FIG. 11, which shows loss of liposome marker during the 24-hour period after intravenous liposome injection. The percent marker remaining at 24 hours is about 3.9 percent for polylactic acid (solid squares), and about 6% for polyglycolic acid (open triangles) These values compare with the 0.1-1% retention seen in conventional liposomes after 24 hours.

The data relating to both blood/RES ratios and to liposome retention time in the bloodstream which were obtained from an model animal system can be reasonably extrapolated to humans and veterinary animals of interest. This is because uptake of liposomes by liver and spleen has been found to occur at similar rates in several mammalian species, including mouse, rat monkey, and human (Gregoriadis, 1974; Kimelberg, 1976; Juliano; Richardson; Lopez-Berestein). This result likely reflects the fact that the biochemical factors which appear to be most important in liposome uptake by the RES—including opsinization by serum lipoproteins, size-dependent uptake effects, and cell shielding by surface moieties—are common features of all mammalian species which have been examined

B. Compound Release in the Bloodstream

In addition to long circulating halflives, another important property of the liposomes of the present invention is the ability to release entrapped compound, at a therapeutically effective dose rate in the bloodstream.

As discussed above, the liposome size between 0.1 and 0.4 microns allows relatively high compound loading in the liposomes, for effective compound release in the bloodstream even at relatively low liposome concentrations. This is typically an important consideration since the total quantity of liposomes which can be administered will be limited, due to the unavoidable presence of some free compound in an injected preparation.

Figure 14:
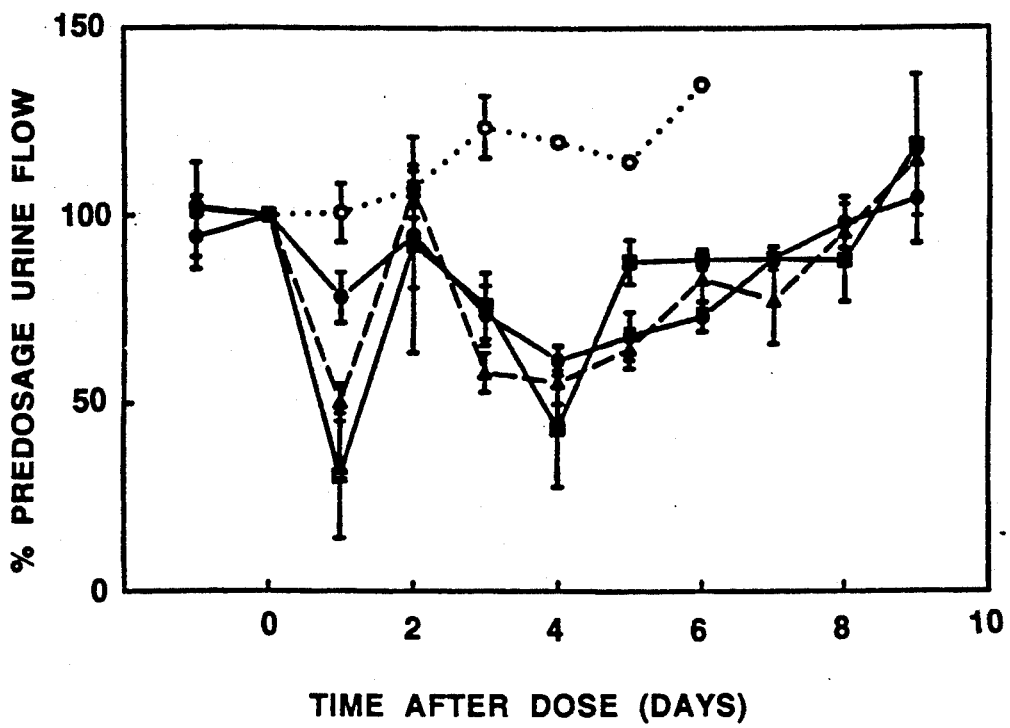
FIG. 14 shows urine flow rates in rats, as a percentage of predosage rate, after surgery and IV administration of saline (control, open circles) and of PEG-liposomes containing entrapped vasopressin at a total dose of 8 μg and mole percent of cholesterol in the liposomes of 33% (closed circles), 16% (closed triangles), and 0% (closed squares)

Another consideration is the ability of an entrapped compound to be released from the liposomes during circulation in the bloodstream. This feature is illustrated in the studies described in Example 15 below. Here PEG-liposomes containing entrapped vasopressin (a 1 kilodalton peptide) were prepared with increasing concentrations of cholesterol, from 0 to about 30 mole percent. In vitro measurements of peptide release from the liposomes in serum indicated that substantially less peptide is released with greater amounts of cholesterol. The rate of release of the peptide hormone in vivo was determined by its diuretic effect, as measured by decreased urine output, in a period 1–8 days following intravenous administration of the liposomes. Details of the study are given in Example 15. As seen in FIG. 14, the short-term effect on urine flow was dependent on cholesterol content, the PEG-liposomes with highest cholesterol producing the greatest hormone effect. Similarly, in the period 2–8 days following IV administration of the liposomes, the two PEG-liposome formulations having the lowest cholesterol concentration gave the greatest hormone effect, indicating higher release rates from the liposomes.

Figure 15:
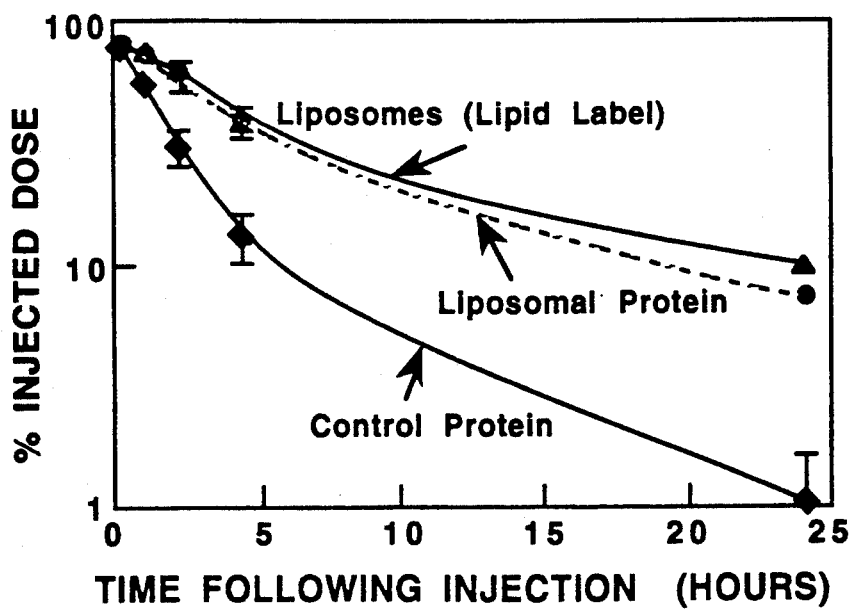
FIG. 15 shows the blood clearance kinetics of free macrophage-colony stimulating factor (M-CSF) (solid triangles), PEG-liposomes containing 30 mole percent cholesterol (solid triangles), and M-CSF associated with the PEG-liposomes (solid circles)

The study reported in Example 16 demonstrates a similar ability to control release rates of large proteins from long-circulating liposomes. Here PEG-liposomes containing encapsulated M-CSF (a 55 kilodalton protein) were examined for percent retention in the bloodstream, of both lipid and protein components. The data plotted in FIG. 15 show liposome lipid (solid triangles) and protein (solid circles) kinetics during a 24-hour period after IV injection for a PEG-lipsome formulation containing 30 mole percent cholesterol. The data indicate about 20% loss of encapsulated material over 24 hours, as discussed in Example 16.

Figure 16:
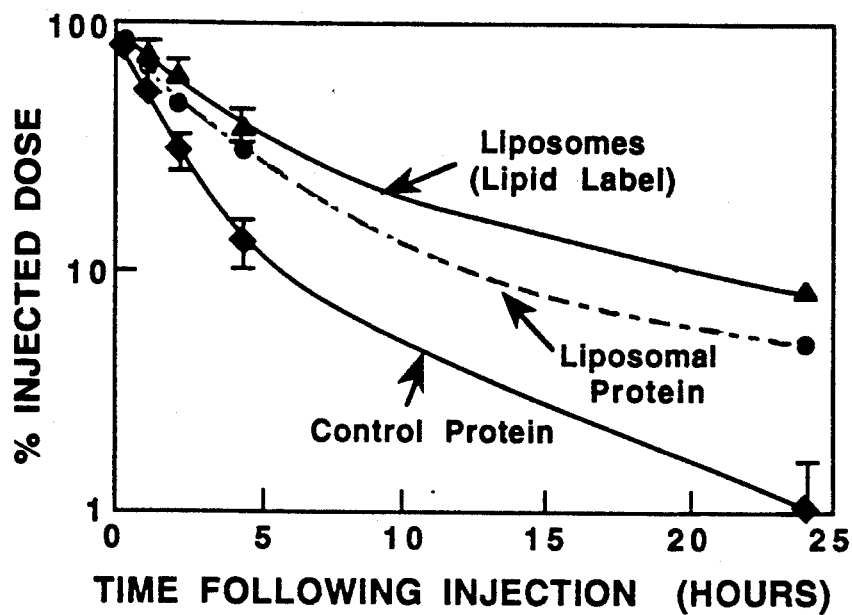
FIG. 16 shows the blood clearance kinetics of free M-CSF (solid triangles), cholesterol-free PEG-liposomes (solid triangles), and M-CSF associated with the PEG-liposomes (solid circles)
Figure 17:
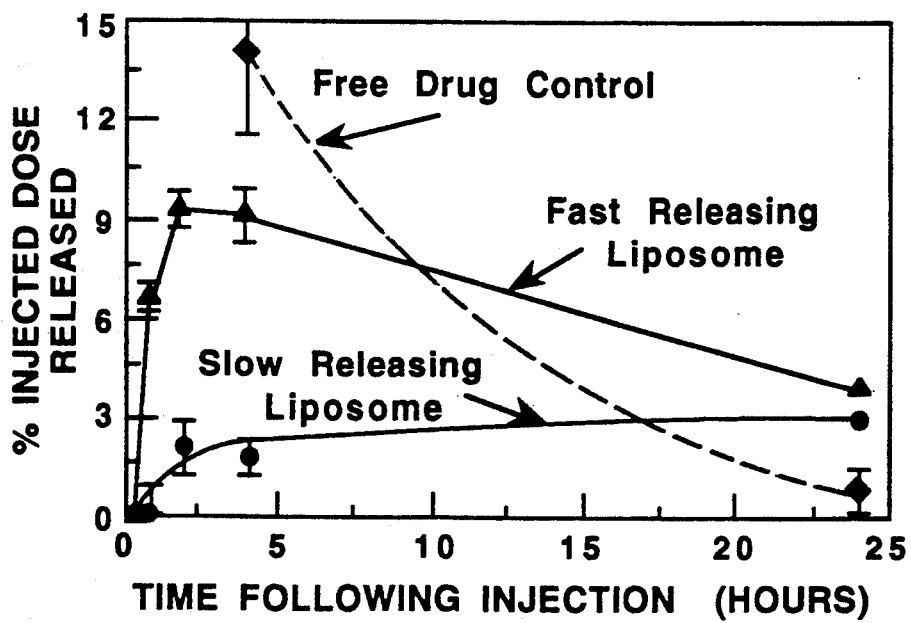
FIG. 17 is a plot of percent release of M-CSF into the blood from PEG liposomes containing 30 (solid circles) and 0 (solid triangles) mole percent cholesterol.

FIG. 16 shows a similar plot for PEG-liposomes without cholesterol. The data here show a 40–50% loss of M-CSF after 24 hours. When lipid and protein markers are normalized at the first time point (15 min) over the plots of relative protein release from cholesterol (solid circles) and no-cholesterol (solid triangles) PEG-liposomes are obtained. The plots illustrate the markedly different protein release kinetics which can be obtained with long circulating liposomes, by varying cholesterol content of the liposomes. Another feature of the data, shown in FIG. 17, is the relatively high percent (at least 3%) of initially injected protein which is released by the 24-hour time point for both formulations.

IV. Intravenous Liposome Treatment

The invention includes, in one aspect, a method for extending to at least 24 hours, the period of effective activity of an therapeutic compound administered as a single bolus injection. The compound is one which can be administered intravenously in a therapeutically effective amount, and which has a halflife in the bloodstream, in free form, of less than about 4 hours.

In practicing the method, there is provided a liposome composition such as described above, containing the compound in liposome-entrapped form. The size, lipid composition, and extent of compound loading of the drug are selected, according to the desired release rates and total release times, as considered in Section III above.

The composition is injected intravenously to a subject at a dose which contains an amount of the compound which is at least 3, and typically 5–20 times the amount of drug that is therapeutically effective as a single dose. Thus, for example, if a therapeutically effective single dose of a compound is 10 $\mu$g/Kg body weight, the liposome composition would be injected at a liposome dose of at least 30 $\mu$g compound/Kg, and typically between 50–200 $\mu$g compound/Kg body weight. As noted above, the amount of material which can be injected is generally limited by the maximum tolerated dose of free compound, since 5–20% or more of the compound may be in free (non-entrapped) form when the composition is administered. Thus, for example, if the maximum tolerated dose of a compound in free form is 2 $\mu$g/Kg body weight, and the liposome composition contains 10% non-entrapped compound, the highest dose of liposome composition which can be given is 20 $\mu$g/Kg body weight.

Studies on the treatment of L1210 leukemia in mice with cytosine arabinoside (araC), in free form and entrapped in PEG-liposomes indicates that the liposome composition produced about a 250–300% increase in survival time when administered in PEG-liposomal form, compared with about a 120% increase in survival time for the drug in free form.

Figure 12:
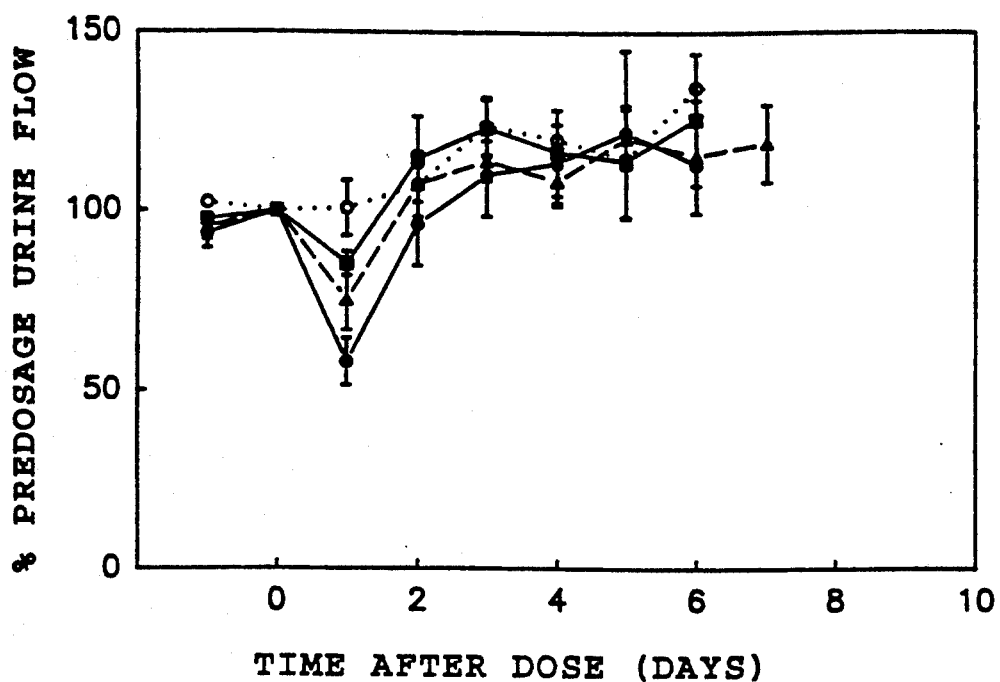
FIG. 12 shows urine flow rates in rats, as a percentage of predosage rate, after surgery and IV administration of saline (control, open circles) and of aqueous solutions of vasopressin at total doses of 0.2 g (closed squares), 0.8 μg (closed triangles), and 2 μg (closed circles)

The ability to achieve long drug release times, on the order of several days, by the method of the invention is illustrated by the studies on IV vasopressin administration reported in Examples 13–15. The studies were carried on Brattle-boro rats which are genetically vasopressin-deficient and thus exhibit symptoms of diabetes incipitus (i.e., high urine flow and low urine osmolarity). FIG. 12 shows the dose effect, measured in percent predosage urine flow, of IV injection of free vasopressin at dose levels of 0.2 $\mu$g (solid squares), 0.8 $\mu$g (solid triangles) and 2.0 $\mu$g (solid circles). The reduction in urine flow is maximum after 1 day, but returns to control levels in all three cases (open circles) by day 2.

Figure 13:
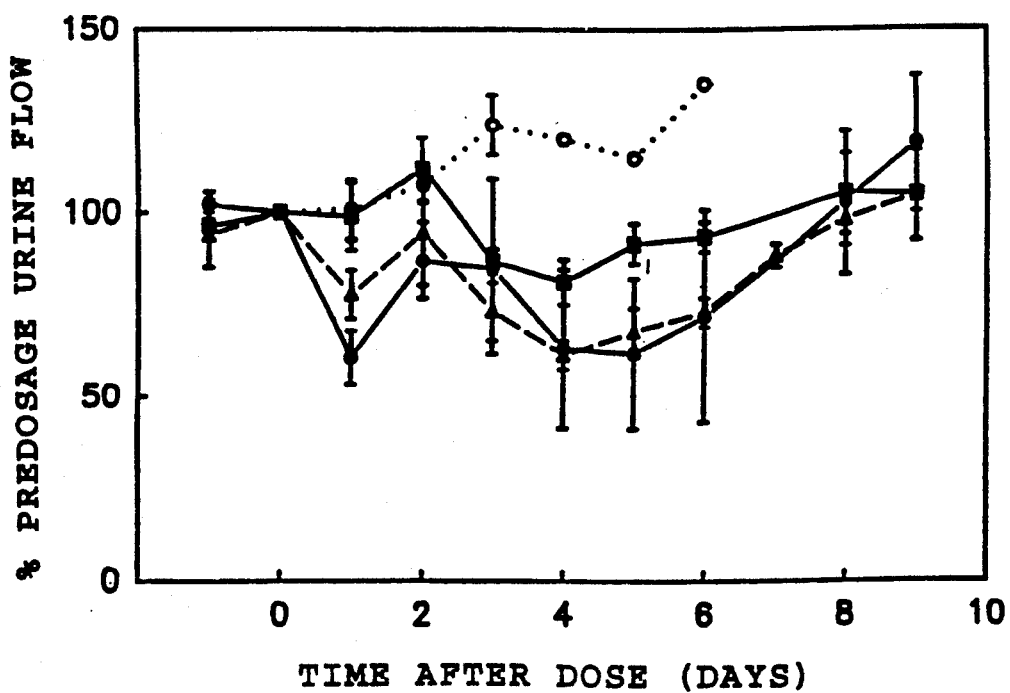
FIG. 13 shows urine flow rates in rats, as a percentage of predosage rate, after surgery and IV administration of saline (control, open circles) and of PEG-liposomes containing entrapped vasopressin at total doses of 2 μg (closed squares), 8 μg (closed tiangles), and 24 μg (closed circles)

FIG. 13 shows the effect on urine flow by vasopressin administered IV in PEG-liposomes, at dosage levels of 2 $\mu$g (solid squares), 8 $\mu$g (solid triangles) and 24 $\mu$g (solid circles). A pronounced reduction in urine flow was observed within one day, with a slight rebound toward control values by day 2—an effect likely due, in part, to free peptide in the liposome formulation. In addition, a marked reduction in urine flow was observed for at least 7 days following IV administration. It is noted that the long-term therapeutic effect is saturated at an 8 g dose, with no further effect observed at 24 $\mu$g. The same long-term therapeutic effect of vasopressin was observed in PEG-liposomes containing various amounts of cholesterol, as seen in FIG. 14, and as discussed above. The data in this figure also illustrate increased short-term (1–2 days) and decreased long-term (2–8 days) effect seen with low cholesterol liposomes having the highest peptide release rates.

More generally, it will be appreciated that a variety of polypeptides which are active in the picogram-to-nanogram/ml range may be administered over a several-day period by the method of the invention. The data presented in FIGS. 15–17, for example, demonstrate that (a) large proteins may be sequestered in the bloodstream, for slow release in therapeutic amounts over an extended period and (b) the rate of release of the protein into the bloodstream can be selectively controlled by liposome composition.

V. Subcutaneous Liposome Treatment

In accordance with another aspect of the invention, it has been discovered that the long-live liposome composition of the invention is also effective for slow release of a liposome-entrapped compound from a subcutaneous (SubQ) site into the bloodstream. In particular, it has been discovered that therapeutic effects of up to 3 weeks or more can be achieved by a single subcutaneous injection of the liposome composition of the invention.

Figure 18A:
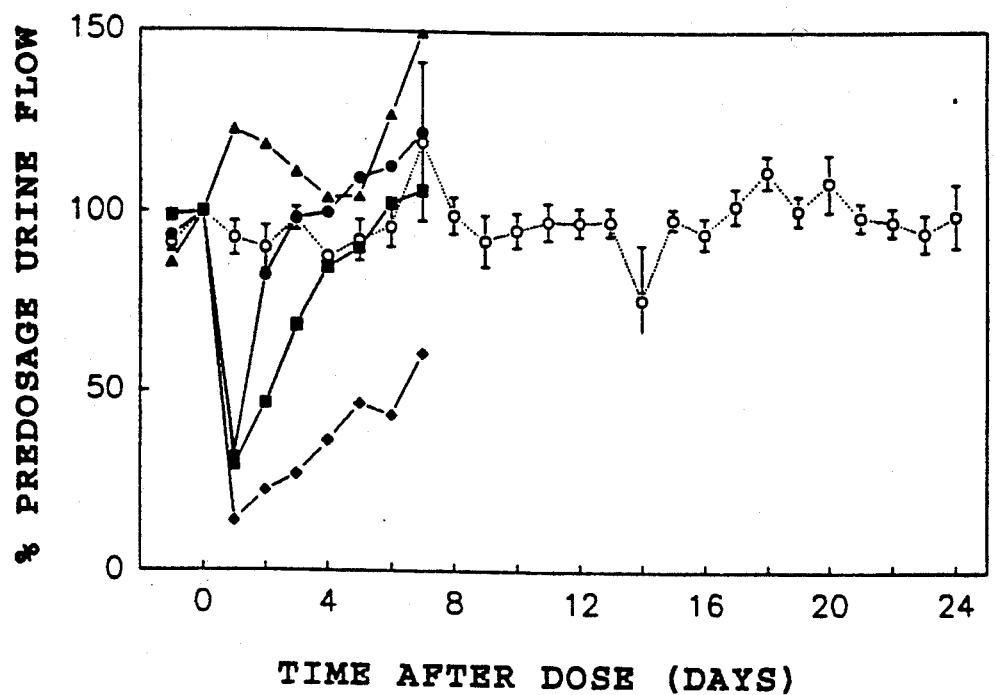
FIG. 18A shows urine flow rates in rats, as a percentage of predosage rate, after surgery and subcutaneous administration of saline (control, open circles) and free vasopressin, in an amount 2 μg (solid triangles), 25 μg (solid circles), and 50 μg (solid squares), and 100 μg (solid diamonds)

The experimental model used to demonstrate this method is the vasopressin model described above, and detailed in Example 17. Briefly, a treatment method involving SubQ injection of free vasopressin was compressed, for duration of physiological effect, with vasopressin administered SubQ in PEG-liposomes. FIG. 18A shows the depression in urine production observed with SubQ administration of free vasopressin at doses of 2 $\mu$g (solid triangles), 25 $\mu$g (solid circles), 50 $\mu$g (solid squares), and 100 $\mu$g (solid diamonds). With the higher doses, a pronounced reduction in urine production at day 1 was observed, with a rebound to control levels (open circles) by day 7. An even longer effect, of at least 24 days, was observed at a dose of 400 $\mu$g (closed squares).

The treatment method employing vasopressin is designed for treatment of diabetes insipidus, by long-term administration of vasopressin from a SubQ site. More generally, the method is designed for extending to at least one week, the period of effective activity of an therapeutic compound which can be administered intravenously in a therapeutically effective amount. The method utilizes liposomes (i) composed of vesicle-forming lipids and between 1-20 mole percent of a vesicle-forming lipid derivatized with a hydrophilic polymer, and (ii) having a selected mean particle diameter in the size range preferably between about 0.07-0.15 microns, and having the compound in liposome-entrapped form.

The liposome composition is administered subcutaneously at a dose of the composition which contains an amount of the liposome-entrapped compound which is at least ten times the therapeutically effective intravenously administered amount.

For compounds, such as vasopressin, which are active in the bloodstream in the picogram-to-nanogram/ml concentration, such as a variety of peptide and proteins, the method can be used for therapeutic delivery of the compound over a several-week period.

The ability of the liposome composition of the invention to produce a long-term therapeutic effect from a SubQ site suggests that the liposomes taken up from this site through the lymphatics may be able to successfully evade the normal lymphatic clearance mechanisms, including dendritic cells. This mechanism is supported by studies on araC administration by the interperitoneal (IP) route by PEG-liposomes. Briefly, it was found that PEG-liposomes containing entrapped araC and administered by IP route produced a 250-300% increase in survival in animals having L1210 leukemias, compared with about 120% increase in survival with the free drug given by the IP route. The results suggests that PEG-liposomes are capable of migrating from the peritoneum through the lymphatics into the bloodstream.

The following examples are intended to illustrate, but not limit, the scope of the invention.

Materials

Cholesterol (Chol) was obtained from Sigma (St. Louis, Mo.). Sphingomyelin (SM), egg phosphatidylcholine (lecithin or PC), partially hydrogenated PC having the composition IV40, IV30, IV20, IV10, and IV1, phosphatidylglycerol (PG), phosphatidylethanolamine (PE), dipalmitoyl-phosphatidyl glycerol (DPPG), dipalmitoyl PC (DPPC), dioleyl PC (DOPC) and distearoyl PC (DSPC) were obtained from Avanti Polar Lipids (Birmingham, Ala.) or Austin Chemical Co (Chicago, Ill.).

[$^{125}$I]-tyraminyl-inulin was made according to published procedures. Gallium citrate was supplied by NEN Neoscan (Boston, Mass.). Vasopressin and macrophage colony stimulating factor were obtained from Sigma (St. Louis, Mo.), and Cetus (Emeryville, Calif.), respectively.

EXAMPLE 1

Preparation of PEG-PE Linked by Cyanuric Chloride

A. Preparation of activated PEG 2-0-Methoxypolyethylene glycol 1900-4,6-dichloro-1,3,5 triazine previously called activated PEG was prepared as described in *J. Biol. Chem.*, 252:3582 (1977) with the following modifications.

Cyanuric chloride (5.5 g; 0.03 mol) was dissolved in 400 ml of anhydrous benzene containing 10 g of anhydrous sodium carbonate, and PEG-1900 (19 g; 0.01 mol) was added and the mixture was stirred overnight at room temperature The solution was filtered, and 600 ml of petroleum ether (boiling range, 35-60°) was added slowly with stirring. The finely divided precipitate was collected on a filter and redissolved in 400 ml of benzene. The precipitation and filtration process was repeated several times until the petroleum ether was free of residual cyanuric chloride as determined by high pressure liquid chromatography on a column (250×3.2 mm) of 5-m "LiChrosorb" (E. Merck), developed with hexane, and detected with an ultraviolet detector Titration of activated PEG-1900 with silver nitrate after overnight hydrolysis in aqueous buffer at pH 10.0, room temperature, gave a value of 1.7 mol of chloride liberated/mol of PEG.

TLC analysis of the product was effected with TLC reversed-phase plates obtained from Baker using methanol:water, 4:1 (v/v) as developer and exposure to iodine vapor for visualization. Under these conditions, the starting methoxy polyglycol 1900 appeared at $R_i=0.54$ to 0.60. The activated PEG appeared at $R_f=0.41$. Unreacted cyanuric chloride appeared at $R_f=0.88$ and was removed.

The activated PEG was analyzed for nitrogen and an appropriate correction was applied in selecting the quantity of reactant to use in further synthetic steps. Thus, when the product contained only 20% of the theoretical amount of nitrogen, the quantity of material used in the next synthetic step was increased by 100/20, or 5-fold. When the product contained 50% of the theoretical amount of nitrogen, only 100/50 or a 2-fold increase was needed.

B. Preparation of N-(4-Chloro-polyglycol 1900)-1,3,5-triazinyl egg phosphatidylethanolamine.

In a screw-capped test tube, 0.74 ml of a 100 mg/ml (0.100 mmole) stock solution of egg phosphatidylethanolamine in chloroform was evaporated to dryness under a stream of nitrogen and was added to the residue of the activated PEG described in section A, in the amount to provide 205 mg (0.100 mmole). To this mixture, 5 ml anhydrous dimethyl formamide was added. 27 microliters (0.200 mmole) triethylamine was added to the mixture, and the air was displaced with nitrogen gas. The mixture was heated overnight in a sand bath maintained at 110° C.

The mixture was then evaporated to dryness under vacuum and a pasty mass of crystalline solid was obtained This solid was dissolved in 5 ml of a mixture of 4 volumes of acetone and 1 volume of acetic acid. The resulting mixture was placed at the top of a 21 mm ×240 mm chromatographic absorption column packed with silica gel (Merck Kieselgel 60, 70–230 mesh) which had first been moistened with a solvent composed of acetone acetic acid, 80/20; v/v.

The column chromatography was developed with the same solvent mixture, and separate 20 to 50 ml aliquots of effluent were collected. Each portion of effluent was assayed by TLC on silica gel coated plates, using 2-butanone/acetic acid/water; 40/25/5; v/v/v as developer and iodine vapor exposure for visualization. Fractions containing only material of $R_f$=about 0.79 were combined and evaporated to dryness under vacuum. Drying to constant weight under high vacuum afforded 86 mg (31.2 micromoles) of nearly colorless solid N-(4-chloro-polyglycol 1900)-1,3,5-triazinyl egg phosphatidylethanolamine containing phosphorous.

The solid compound was taken up in 24 ml of ethanol/chloroform; 50/50 chloroform and centrifuged to remove insoluble material. Evaporation of the clarified solution to dryness under vacuum afforded 21 mg (7.62 micromoles) of colorless solid.

EXAMPLE 2

Preparation of the Carbamate-Linked PEG-PE

A. Preparation of the imidazole carbamate of polyethylene glycol methyl ether 1900

9.5 grams (5 mmoles) of polyethylene glycol methyl ether 1900 obtained from Aldrich Chemical Co. was dissolved in 45 ml benzene which has been dried over molecular sieves. 0.89 grams (5.5 mmoles) of pure carbonyl diimidazole was added. The purity was checked by an infra-red spectrum. The air in the reaction vessel was displaced with nitrogen. Vessel was enclosed and heated in a sand bath at 75° C. for 16 hours.

The reaction mixture was cooled and the clear solution formed at room temperature. The solution was diluted to 50.0 ml with dry benzene and stored in the refrigerator as a 100 micromole/ml stock solution of the imidazole carbamate of PEG ether 1900.

B. Preparation of the phosphatidylethanolamine carbamate of polyethylene glycol methyl ether 1900

10.0 ml (1 mmol) of the 100 mmol/ml stock solution of the imidazole carbamate of polyethylene glycol methyl ether 1900 (compound X) was pipetted into a 10 ml pear-shaped flask. The solvent was removed under vacuum. 3.7 ml of a 100 mg/ml solution of egg phosphatidyl ethanolamine (V) in chloroform (0.5 mmol) was added. The solvent was evaporate under vacuum. 2 ml of 1,1,2,2-tetrachloroethylene and 139 microliters (1.0 mmol) of triethylamine VI was added. The vessel was closed and heated in a sand bath maintained at 95° C. for 6 hours. At this time, thin-layer chromatography was performed with fractions of the above mixture to determine an extent of conjugation on SiO2 coated TLC plates, using butanone/acetic acid/water; 40/5/5; v/v/v; was performed as developer Iodine vapor visualization revealed that most of the free phosphatidyl ethanolamine of Rf=0.68, had reacted, and was replaced by a phosphorous-containing lipid at $R_f$=0.78 to 0.80.

The solvent from the remaining reaction mixture was evaporated under vacuum. The residue was taken up in 10 ml methylene chloride and placed at the top of a 21 mm×270 mm chromatographic absorption column packed with Merck Kieselgel 60 (70–230 mesh silica gel), which has been first rinsed with methylene chloride. The mixture was passed through the column, in sequence, using the following solvents

TABLE 1

| ml | Volume % of Methylene Chloride | Volume % Methanol With 2% Acetic Acid |
|---|---|---|
| 100 | 100% | 0% |
| 200 | 95% | 5% |
| 200 | 90% | 10% |
| 200 | 85% | 15% |
| 200 | 60% | 40% |

50 ml portions of effluent were collected and each portion was assayed by TLC on SiO2—coated plates, using 12 vapor absorption for visualization after development with chloroform/methanol/water/concentrated ammonium hydroxide; 130/70/8/0.5%; v/v/v/v. Most of the phosphates were found in fractions 11, 12, 13 and 14.

These fractions were combined, evaporated to dryness under vacuum and dried in high vacuum to constant weight. They yielded 669 mg of colorless wax of phosphatidyl etha-nolamine carbamate of polyethylene glycol methyl ether. This represented 263 micromoles and a yield of 52.6% based on the phosphatidyl ethanolamine.

An NMR spectrum of the product dissolved in deuterochloroform showed peaks corresponding to the spectrum for egg PE, together with a strong singlet due to the methylene groups of the ethylene oxide chain at Delta=3.4 ppm. The ratio of methylene protons from the ethylene oxide to the terminal methyl protons of the PE acyl groups was large enough to confirm a molecular weight of about 2000 for the polyethylene oxide portion of the molecule of the desired product polyethylene glycol conjugated phosphatidyethanolamine carbamate, M.W. 2,654.

EXAMPLE 3

Preparation of Ethylene-Linked PEG-PE

A. Preparation of I-trimethylsilyloxy-polyethylene glycol is illustrated in Reaction Scheme 3A 15.0 gm (10 mmoles) of polyethylene glycol) M.Wt. 1500, (Aldrich Chemical) was dissolved in 80 ml benzene. 1.40 ml (11 mmoles) of chlorotrimethyl silane (Aldrich Chemical Co.) and 1.53 ml (1 mmoles) of triethylamine was added. The mixture was stirred at room temperature under an inert atmosphere for 5 hours.

The mixture was filtered with suction to separate crystals of triethylammonium chloride and the crystals were washed with 5 ml benzene. Filtrate and benzene wash liquids were combined. This solution was evaporated to dryness under vacuum to provide 15.83 grams of colorless oil which solidified on standing.

TLC of the product on Si-$C_{18}$ reversed-phase plates using a mixture of 4 volumes of ethanol with 1 volume of water as developer, and iodine vapor visualization, revealed that all the polyglycol 1500 ($R_f$=0.93) has been consumed, and was replaced by a material of $R_f$=0.82. An infra-red spectrum revealed absorption peaks characteristic only of polyglycols.

Yield of I-trimethylsilyoxypolyethylene glycol, M.W. 1500 was nearly quantitative.

B. Preparation of trifluoromethane sulfonyl ester of I1trimethylsilyloxy-polyethylene glycol 15.74 grams (10 mmol) of the crystalline I-trimethylsilyloxy polyethylene glycol obtained above was dissolved in 40 ml anhydrous benzene and cooled in a bath of crushed ice. 1.53 ml (11 mmol) triethylamine and 1.85 ml (11 mmol) of trifluoromethanesulfonic anhydride obtained from Aldrich Chemical Co. were added and the mixture was stirred over night under an inert atmosphere until the reaction mixture changed to a brown color.

The solvent was then evaporated under reduced pressure and the residual syrupy paste was diluted to 100.0 ml with methylene chloride. Because of the great reactivity of trifluoromethane sulfonic esters, no further purification of the trifluoromethane sulfonyl ester of I-trimethylsilyloxy polyethylene glycol was done.

C. Preparation of N-1-trimethylsilyloxy polyethylene glycol 1500

10 ml of the methylene chloride stock solution of the trifluoromethane sulfonyl ester of 1-trimethylsilyloxy polyethylene glycol was evaporated to dryness under vacuum to obtain about 1.2 grams of residue (approximately 0.7 mmoles). To this residue, 3.72 ml of a chloroform solution containing 372 mg (0.5 mmoles) egg PE was added. To the resulting solution, 139 microliters (1.0 mmole) of triethylamine was added and the solvent was evaporated under vacuum. To the obtained residue, 5 ml dry dimethyl formamide and 70 microliters (0.50 mmoles) triethylamine was added. Air from the reaction vessel was displaced with nitrogen. The vessel was closed and heated in a sand bath 110° C. for 22 hours. The solvent was evaporated under vacuum to obtain 1.58 grams of brownish-colored oil. A 21×260 mm chromatographic absorption column filled with Kieselgel 60 silica 70–230 mesh, was prepared and rinsed with a solvent composed of 40 volumes of butanone, 25 volumes acetic acid and 5 volumes of water. The crude product was dissolved in 3 ml of the same solvent and transferred to the top of the chromatography column. The chromatogram was developed with the same solvent and sequential 30 ml portions of effluent were assayed each by TLC.

The TLC assay system used silica gel coated glass plates, with solvent combination butanone/acetic acid/water; 40/25/5; v/v/v. Iodine vapor absorption served for visualization. In this solvent system, the N-1-trimethylsilyloxy polyethylene glycol 1500 PE appeared at $R_f$=0.78. Unchanged PE appeared at $R_f$=0.68.

The desired N-1-trimethylsilyloxy polyethylene glycol 1500 PE was a chief constituent of the 170–300 ml portions of column effluent. When evaporated to dryness under vacuum these portions afforded 111 mg of pale yellow oil of compound.

D. Preparation of N-polyethylene glycyl 1500: phosphatidyl-ethanolamine acetic acid deprotection Once-chromatographed, PE .compound was dissolved in 2 ml of tetrahydrofuran. To this, 6 ml acetic acid and 2 ml water was added. The resulting solution was let to stand for 3 days at 23° C. The solvent from the reaction mixture was evaporated under vacuum and dried to constant weight to obtain 75 mg of pale yellow wax. TLC on Si-C18 reversed-phase plates, developed with a mixture of 4 volumes ethanol, 1 volume water, indicated that some free PE and some polyglycol-like material formed during the hydrolysis.

The residue was dissolved in 0.5 ml tetrahydrofuran and diluted with 3 ml of a solution of ethanol water; 80:20; v:v. The mixture was applied to the top of a 10 mm X 250 mm chromatographic absorption column packed with octadecyl bonded phase silica gel and column was developed with ethanol water 80:20% by volume, collecting sequential 20 ml portions of effluent. The effluent was assayed by reversed phase TLC. Fractions containing only product of P=0.08 to 0.15 were combined. This was typically the 20–100 ml portion of effluent. When evaporated to dryness, under vacuum, these portions afforded 33 mg of colorless wax PEG-PE corresponding to a yield of only 3%, based on the starting phosphatidyl ethanolamine.

NMR analysis indicated that the product incorporated both PE residues and polyethylene glycol residues, but that in spite of the favorable-appearing elemental analysis, the chain length of the polyglycol chain has been reduced to about three to four ethylene oxide residues. The product prepared was used for a preparation of PEG-PE liposomes.

E. Preparation of N-Polyethylene glycol 1500 P.E. by fluoride deprotection 500 mg of crude N-1-trimethylsilyloxy polyethylene glycol PE was dissolved in 5 ml tetrahydrofuran and 189 mg (0.600 millimoles) of tetrabutyl ammonium fluoride was added and agitated until dissolved. The reactants were let to stand over night at 20° C.

The solvent was evaporated under reduced pressure and the residue was dissolved in 10 ml chloroform, washed with two successive 10 ml portions of water, and centrifuged to separate chloroform and water phases. The chloroform phase was evaporated under vacuum to obtain 390 mg of orange-brown wax, which was determined to be impure N-polyethylene glycol 1500 PE compound.

The wax was re-dissolved in 5 ml chloroform and transferred to the top of a 21×270 mm column of silica gel moistened with chloroform. The column was developed by passing 100 ml of solvent through the column. The Table 2 solvents were used in sequence:

TABLE 2

| Volume % Chloroform | Volume % Methanol Containing 2% Conc. Ammonium Hydroxide/methanol |
| --- | --- |
| 100% | 0% |
| 95% | 5% |
| 90% | 10% |
| 85% | 15% |
| 80% | 20% |
| 70% | 30% |
| 60% | 40% |

TABLE 2-continued

| Volume % Chloroform | Volume % Methanol Containing 2% Conc. Ammonium Hydroxide/methanol |
|---|---|
| 50% | 50% |
| 0% | 100% |

Separated 50 ml fractions of column effluent were saved. The fractions of the column were separated by TLC on Si-C18 reversed-phase plates. TLC plates were developed with 4 volumes of ethanol mixed with 1 volume of water. Visualization was done by exposure to iodine vapor.

Only those fractions containing an iodine-absorbing lipid of $R_f$ about 0.20 were combined and evaporated to dryness under vacuum and dried in high vacuum to constant weight. In this way 94 mg of waxy crystalline solid was obtained of M.W. 2226. The proton NMR spectrum of this material dissolved in deuterochloroform showed the expected peaks due to the phosphatidyl ethanolamine portion of the molecule, together with a few methylene protons attributable to polyethylene glycol. (Delta=3.7).

EXAMPLE 4

Preparation of PE-Hydrophylic Polymers

A. Preparation of PE polyactic acid 200 mg. (0.1 mmoles) poly (lactic acid), m. wt.=2,000 (ICN, Cleveland, Ohio) was dissolved in 2.0 ml dimethyl sulfoxide by heating while stirring to dissolve the material completely. Then the solution was cooled immediately to 65° C. and poured onto a mixture of 75 mg (0.1 mmoles) of distearylphosphatidyl-ethanolamine (Cal. Biochem, La Jolla) and 41 mg (0.2 mmoles) dicyclohexylcarbodiimide (DCCI). Then 28 ml (0.2 mmoles) of triethylamine was added, the air swept out of the tube with nitrogen gas, the tube capped, and heated at 65° C. for 48 hours.

After this time, the tube was cooled to room temperature, and 6 ml of chloroform added. The chloroform solution was washed with three successive 6 ml volumes of water, centrifuged after each wash, and the phases separated with a Pasteur pipette. The remaining chloroform phase was filtered with suction to remove suspended distearolyphosphatidyl-ethanolamine. The filtrate was dried under vacuum to obtain 212 mg of semi-crystalline solid.

This solid was dissolved in 15 ml of a mixture of 4 volumes ethanol with 1 volume water and passed through a 50 mm deep and 21 mm diameter bed of H. Dowex 50 cation exchange resin, and washed with 100 ml of the same solvent.

The filtrate was evaporated to dryness to obtain 131 mg colorless wax. 291 mg of such wax was dissolved in 2.5 ml chloroform and transferred to the top of a 21 mm×280 mm column of silica gel wetted with chloroform. The chromatogram was developed by passing through the column, in sequence, 100 ml each of:

100% chloroform, 0% (1% NH$_4$OH in methanol);
90% chloroform, 10% (1% NH$_4$OH in methanol);
85% chloroform, 15% (1% NH$_4$OH in methanol);
80% chloroform, 20% (1% NH$_4$OH in methanol);
70% chloroform, 30% (1% NH$_4$OH in methanol);

Individual 25 ml portions of effluent were saved and assayed by TLC on SFO$_2$-coated plates, using CHCl$_3$, CH$_3$OH, H$_2$O, con. NH$_4$OH, 130, 70, 8, 0.5 v/v as developer and I$_2$ vapor absorption for visualization. The 275-325 ml portions of column effluent contained a single material, PO$_4$+, of $R_f$=0.89. When combined and evaporated to dryness, these afforded 319 mg colorless wax.

Phosphate analysis agrees with a molecular weight of possibly 115,000. Apparently, the polymerization of the poly (lactic acid) occurred at a rate comparable to that at which it reacted with phosphatidylethanolamine. This side-reaction could probably be minimized by working with more dilute solutions of the reactants.

B. Preparation of poly (glycolic acid) amide of DSPE

A mixture of 266 mg. (3.50 mmoles) glycolic acid, 745 mg (3.60 mmoles) dicyclohexyl carbodiimide, 75 mg. (0.10 mmoles) distearoyl phosphatidyl ethanolamine, 32 microliters (0.23 mmoles triethyl amine, and 5.0 ml dry dimethyl sulfoxide was heated at 75° C., under a nitrogen atmosphere, cooled to room temperature, then diluted with an equal volume of chloroform, and then washed with three successive equal volumes of water to remove dimethyl sulfoxide. Centrifuge and separate phases with a Pasteur pipette each time.

Filter the chloroform phase with suction to remove a small amount of suspended material and vacuum evaporate the filtrate to dryness to obtain 572 mg. pale amber wax.

Re-dissolve this material in 2.5 ml chloroform and transfer to the top of a 21 mm×270 mm column of silica gel (Merck Hieselgel 60) which has been wetted with chloroform.

Develop the chromatogram by passing through the column, in sequence, 100 ml each of:

100% chloroform, 0% (1% NH$_4$OH in methanol);
90% chloroform, 10% (1% NH$_4$OH in methanol);
85% chloroform, 15% (1% NH$_4$OH in methanol);
80% chloroform, 20% (1% NH$_4$OH in methanol);
70% chloroform, 30% (1% NH$_4$OH in methanol).

Collect individual 25 ml portions of effluent and assay each by TLC on Si)$_2$-coated plates, using CH Cl$_3$, CH$_3$OH, H$_2$O, con-NH$_4$OH; 130, 70, 8, 0.5 v/v as developer.

Almost all the PO$_4$+material will be in the 275–300 ml portion of effluent. Evaporation of this to dryness under vacuum, followed by high-vacuum drying, affords 281 mg of colorless wax.

Phosphate analysis suggests a molecular weight of 924,000.

Manipulation of solvent volume during reaction and molar ratios of glycolic acid and cicyclohexyl carbodiimide would probably result in other sized molecules.

EXAMPLE 5

Preparation of REVs and MLVs

A. Sized REVs

A total of 15 $\mu$moles of the selected lipid components, in the mole ratios indicated in the examples below, were dissolved in chloroform and dried as a thin film by rotary evaporation. This lipid film was dissolved in 1 ml of diethyl ether washed with distilled water. To this lipid solution was added 0.34 ml of an aqueous buffer solution containing 5 mM Tris, 100 mM NaCl, 0.1 mM EDTA, pH 7.4, and the mixture was emulsified by sonication for 1 minute, maintaining the temperature of the solution at or below room temperature. Where the liposomes were prepared to contain encapsulated [$^{125}$I] tyraminyl-inulin, such was included in the phosphate buffer at a concentration of about 4 $\mu$Ci/ml buffer.

The ether solvent was removed under reduced pressure at room temperature, and the resulting gel was taken up in 0.1 ml of the above buffer, and shaken vigorously. The resulting REV suspension had particle sizes, as determined by microscopic examination, of between about 0.1 to 20 microns, and was composed predominantly of relatively large (greater than 1 micron) vesicles having one or only a few bilayer lamellae.

The liposomes were extruded twice through a polycarbonate filter (Szoke, 1978), having a selected pore size of 0.4 microns or 0.2 microns. Liposomes extruded through the 0.4 micron filter averaged 0.17+ (0.15) micron diameters, and through the 0.2 micron filter, 0.16 (0.05) micron diameters. Non-encapsulated [$^{125}$I] tyraminyl-inulin was removed by passing the extruded liposomes through Sephadex G-50 (Pharmacia).

B. Sized MLVs

Multilamellar vesicle (MLV) liposomes were prepared according to standard procedures by dissolving a mixture of lipids in an organic solvent containing primarily $CHCl_3$ and drying the lipids as a thin film by rotation under reduced pressure. In some cases a radioactive label for the lipid phase was added to the lipid solution before drying. The lipid film was hydrated by addition of the desired aqueous phase and 3 mm glass beads followed by agitation with a vortex and shaking above the phase transition temperature of the phospholipid component for at least 1 hour. In some cases a radioactive label for the aqueous phase was included in the buffer. In some cases the hydrated lipid was repeatedly frozen and thawed three times to provide for ease of the following extrusion step.

The size of the liposome samples was controlled by extrusion through defined pore polycarbonate filters using pressurized nitrogen gas. In one procedure, the liposomes were extruded one time through a filter with pores of 0.4 μm and then ten times through a filter with pores of 0.1 μm. In another procedure, the liposomes were extruded three times through a filter with 0.2 m pores followed by repeated extrusion with 0.05 μm pores until the mean diameter of the particles was below 100 nm as determined by DLS. Unencapsulated aqueous components were removed by passing the extruded sample through a gel permeation column separating the liposomes in the void volume from the small molecules in the included volume.

C. Loading $^{67}$Ga Into DF-Containing Liposomes

The protocol for preparation of Ga$^{67}$-DF labeled liposomes as adapted from known procedures (Gabizon). Briefly, liposomes were prepared with the ion chelator desferal mesylate encapsulated in the internal aqueous phase to bind irreversibly Ga transported through the bilayer by hydroxyquinoline (oxine).

D. Dynamic Light Scattering

Liposome particle size distribution measurements were obtained by DLS using a NICOMP Model 200 with a Brookhaven Instruments BI-2030AT autocorrelator attached. The instruments were operated according to the manufacturer's instructions. The NICOMP results were expressed as the mean diameter and standard deviation of a Gaussian distribution of vesicles by relative volume.

E. Preparation of Sized MLVs by Homogenization

PEG-PE composed of methoxy PEG, molecular weight 1900 and DSPE was prepared as in Example 2. The PEG-PE lipid was combined with and hydrogenated soy PC (HSPC) and cholesterol in a mole ratio of 5:55:40. A total of 60 mg of lipid were hydrated in aqueous buffer solution containing 125 mM ammonium citrate, pH 5.0, to a final volume of 200 ml, and the mixture was homogenized with a Rannie Model Mini-Lab Type 8.30H Homogenizer at a pressure of 8,000 psi at 50° C. The mean particle size of the homogenate was measured by dynamic light scattering using either a Nicomp Model 200 Analyser or a Coulter N4SD Analyser. The reduction in mean particle size, as a function of homogenization time, is shown in FIGS. 19A and 19B, for particle size measurements by the Nicomp and Coulter Analysers, respectively. As seen, particle size reduction stabilized at about 100-150 nm after 3-5 minutes. Under the homogenization conditions employed, the material was cycled through the homogenizer about one time per minute.

EXAMPLE 6

Liposome Blood Lifetime Measurements

A. Measuring Blood Circulation Time and Blood/RES Ratios

In vivo studies of liposomes were performed in two different animal models: Swiss-Webster mice at 25 g each and laboratory rats at 200-300 g each. The studies in mice involved tail vein injection of liposome samples at 1 μM phospholipid/mouse followed by animal sacrifice after a defined time and tissue removal for label quantitation by gamma counting or scintillation counting, depending on the radiolabel used. The weight and percent of the injected dose in each tissue were determined. The studies in rats involved establishment of a chronic catheter in a femoral vein for removal of blood samples at defined times after injection of liposome samples in a catheter in the other femoral artery at 3-4M phospholipid/rat. The percent of the injected dose remaining in the blood at several time points up to 24 hours was determined.

B. Time Course of Liposome Retention in the Bloodstream

PEG-PE composed of methoxy PEG, molecular weight 1900 and 1-palmitoyl-2-oleyl-PE (POPE) was prepared as in Example 2. The PEG-POPE lipid was combined with and partially hydrogenated egg PC (PHEPC) in a lipid:lipid mole ratio of about 0.1:2, and the lipid mixture was hydrated and extruded through a 0.1 micron polycarbonate membrane, as described in Example 4, to produce MLV's with average size about 0.1 micron. The MLV lipids included a small amount of radiolabeled lipid marker $^{14}$C-cholesteryl oleate, and the encapsulated marker $^3$H-inulin and/or $^{67}$Ga-DF as described in Example 5.

The liposome composition was injected and the percent initial injected dose in mice was determined as described in Example 4, at 1, 2, 3, 4, and 24 after injection. The time course of loss of radiolabeled material is seen in FIG. 8 which is a plot of percent injected dose for encapsulated inulin (solid circles), inulin marker corrected to the initial injection point of 100% (open circles), and lipid marker (closed triangles), over a 24-hour period post injection. As seen, both lipid and encapsulated markers showed greater than 10% of original injected dose after 24 hours.

Table 5, and used to form MLV's sized to 0.1 micron as described in Example 4.

TABLE 4

| Egg PC Form | Phase Transition Temperature Range °13 C. | Mole % Fatty Acid Comp. | | | | | | |
|---|---|---|---|---|---|---|---|---|
| | | 18:0 | 18:1 | 18:2 | 20:0 | 20:1-4 | 22:0 | 22:1-6 |
| Native | <0 | 12 | 30 | 15 | 0 | 3 | 0 | 5 |
| IV 40 | <20 | 14 | 32 | 4 | 0 | 3 | 0 | 4 |
| IV 30 | <20-30 | 20 | 22 | 0 | 1 | 2 | 1 | 3 |
| IV 20 | 23-45 | 30 | 10 | 0 | 2 | 1 | 2 | 3 |
| IV 10 | 37-50 | 42 | 4 | 0 | 3 | 1 | 4 | 2 |
| IV 1 | 49-54 | 56 | 0 | 0 | 5 | 0 | 6 | 0 |

C. 24 Hour Blood Liposome Levels

Studies to determine percent injected dose in the blood, and blood/RES ratios of a liposomal marker, 24 hours after intravenous liposome injection, were carried out as described above. Liposome formulations having the compositions shown at the left in Table 3 below were prepared as described above. Unless otherwise noted, the lipid-derivatized PEG was PEG-1900, and the liposome size was 0.1 micron. The percent dose remaining in the blood 24 hours after intravenous administration, and 24-hour blood/RES ratios which were measured are shown in the center and right columns in the table, respectively.

TABLE 3

| Lipid Composition* | 24 Hours After IV Dose | |
|---|---|---|
| | % Injected Dose in Blood | B/RES |
| PG:PC:Chol (.75:9.25:5) | 0.2 | 0.01 |
| PC:Chol (10:5) | 0.8 | 0.03 |
| PEG-DSPE:PC:Chol | 23.0 | 3.0 |
| PEG-DSPE:PC:Chol (250 nm) | 9.0 | 0.5 |
| PEG$_{5000}$-DSPE:PC:Chol | 21.0 | 2.2 |
| PEG$_{750}$-DSPE:PC:Chol | 3.2 | 0.33 |
| PEG$_{120}$-DSPE:PC:Chol | 5.0 | 0.2 |
| PEG-DSPE:PC (0.75:9.25) | 22.0 | 1.7 |
| PEG-DSPE:PG:PC:Chol (0.75:2.25:7:5) | 40.0 | 4.0 |
| PEG-DSPE:NaCholSO$_4$:PC:Chol (0.75:0.75:9.25:4.25) | 25.0 | 2.5 |

*All formulations contain 33% cholesterol and 7.5% charged component and were 100 nm mean diameter except as noted. PEG-DSPE consisted of PEG$_{1900}$ except as noted. Encapsulated $^{67}$Ga-DF was used as the radiolabel and rats were the species tested.

As seen, percent dose remaining in the blood 24 hours after injection ranged between 5-40% for liposomes containing PEG-derivatized lipids. By contrast, in both liposome formulations lacking PEG-derivatized lipids, less than 1% of liposome marker remained after 24 hours. Also as seen in Table 3, blood/RES ratios increased from 0.01-0.03 in control liposomes to at least 0.2, and as high as 4.0 in liposomes containing PEG-derivatized liposomes.

EXAMPLE 7

Effect of Phospholipid Acl-Chain Saturation on Blood/RES Ratios in PEG-PE Liposomes PEG-PE composed of methoxy PEG, molecular weight 1900 and distearylPE (DSPE) was prepared as in Example 2. The PEG-PE lipids were formulated with selected lipids from among sphingomyelin (SM), fully hydrogenated soy PC (PC), cholesterol (Chol), partially hydrogenated soy PC (PHSPC), and partially hydrogenated PC lipids identified as PC IV1, IV10, IV20, IV30, and IV40 in Table 4. The lipid components were mixed in the molar ratios shown at the left in

TABLE 5

| | Blood | RES | B/RES | % Remaining |
|---|---|---|---|---|
| PEG-PE:SM:PC:Chol 0.2:1:1:1 | 19.23 | 6.58 | 2.92 | 49.23 |
| PEG-PE:PHSPC:Chol 0.15:1.85:1 | 20.54 | 7.17 | 2.86 | 55.14 |
| PEG-PE:PC IV1:Chol 0.15:1.85:1 | 17.24 | 13.71 | 1.26 | 60.44 |
| PEG-PE:PC IV1:Chol (two animals) 0.15:1.85:1 | 19.16 | 10.07 | 1.90 | 61.87 |
| PEG-PE:PC IV10:Chol (two animals) 0.15:1.85:1 | 12.19 | 7.31 | 1.67 | 40.73 |
| PEG-PE:PC IV10:Chol 0.15:1.85:1 | 2.4 | 3.5 | 0.69 | 12.85 |
| PEG-PE:PC IV20:Chol 0.15:1.85:1 | 24.56 | 7.52 | 3.27 | 62.75 |
| PEG-PE:PC IV20:Chol 0.15:1.85:1 | 5.2 | 5.7 | 0.91 | 22.1 |
| PEG-PE:PC IV40:Chol 0.15:1.85:1 | 19.44 | 8.37 | 2.19 | 53.88 |
| PEG-PE:PC IV:Chol 0.15:1.85:0.5 | 20.3 | 8.8 | 2.31 | 45.5 |
| PEG-PE:EPC:Chol 0.15:1.85:1 | 15.3 | 9.6 | 1.59 | 45.9 |

24 hours after injection, the percent material injected (as measured by percent of $^{67}$Ga-desferal) remaining the blood and in the liver (L) and spleen (S) were determined, and these values are shown in the two data columns at the left in Table 5. The blood and L+S (RES) values were used to calculate a blood/RES value for each composition. The column at the right in Table 5 shows total amount of radioactivity recovered. The two low total recovery values in the table indicate anomalous clearance behavior.

The results from the table demonstrate that the blood/RES ratios are largely independent of the fluidity, or degree of saturation of the phospholipid components forming the liposomes. In particular, there was no systematic change in blood/RES ratio observed among liposomes containing largely saturated PC components (e.g., IV1 and IV10 PC's), largely unsaturated PC components (IV40), and intermediate-saturation components (e.g., IV20).

In addition, a comparison of blood lifetimes obtained using the relatively saturated PEG-DSPE compound and the relatively unsaturated PEG-POPE compound (Example 5) indicates that the degree of saturation of the derivatized lipid is itself not critical to the ability of the liposomes to evade uptake by the RES.

EXAMPLE 8

Effect of Cholesterol and Ethoxylated Cholesterol on Blood/RES Ratios in PEG-PE Liposomes

A. Effect of added cholesterol

PEG-PE composed of methoxy PEG, molecular weight 1900 and was derivatized with DSPE as described in Example 2. The PEG-PE lipids were formulated with selected lipids from among sphingomyelin (SM), fully hydrogenated soy PC (PC), and cholesterol (Chol), as indicated in the column at the left in Table 6 below. The three formulations shown in the table contain about 30, 15, and 0 mole percent cholesterol. Both REV's (0.3 micron size) and MLV's (0.1 micron size) were prepared, substantially as in Example 4, with encapsulated tritium-labeled inulin.

The percent encapsulated inulin remaining in the blood 2 and 24 hours after administration, given at the right in Table 6 below, show no measurable effect of cholesterol, in the range 0–30 mole percent.

TABLE 6

| | % Injected Dose In Blood | | | |
|---|---|---|---|---|
| | 2 HR. | 24 HR. | 2 HR. | 24 HR. |
| $^3$H-Inulin | $^3$H Aqueous Label (Leakage) | | $^{14}$C- Lipid Label | |
| 1) SM:PC:Chol:PEG-DSPE 1:1:1:0.2 | | | | |
| 100 nm MLV | 19 | 5 | 48 | 24 |
| 300 nm REV | 23 | 15 | 67 | 20 |
| 2) SM:PC:Chol:PEG-DSPE 1:1:0.5:0.2 | | | | |
| 300 nm REV | 23 | 15 | 71 | 17 |
| 3) SM:PC:PEG-DSPE 1:1:0.2 | | | | |
| 100 nm MLV | 19 | 6 | 58 | 24 |
| 300 nm REV | 32 | 23 | 76 | 43 |

B. Effect of ethoxylated cholesterol

Methoxy-ethoxy-cholesterol was prepared by coupling methoxy ethanol to cholesterol via the trifluorosulfonate coupling method described in Section I. PEG-PE composed of methoxy PEG, molecular weight 1900 and was derivatized to DSPE as described in Example 2. The PEG-PE lipids were formulated with selected lipids from among distearylPC (DSPC), hydrogenated soy PC (HSPC), cholesterol, and ethoxylated cholesterol, as indicated at the left in Table 7. The data show that (a) ethoxylated cholesterol, in combination with PEG-PE, gives about the same degree of enhancement of liposome lifetime in the blood as PEG-PE alone. By itself, the ethoxylated cholesterol provides a moderate degree of enhancement of liposome lifetime, but substantially less than that provided by PEG-PE.

TABLE 7

| | % Injected Dose In Blood $^{14}$C-Chol-Oleate | |
|---|---|---|
| Formulation | 2 HR. | 24 HR. |
| HSPC:Chol:PEG-DSPE 1.85:1:0.15 | 55 | 9 |
| HSPC:Chol:PEG-DSPE:PEG$_5$-Chol 1.85:0.85:0.15:0.15 | 57 | 9 |
| HSPC:Chol:HPC:PEG$_5$-Chol 1.85:0.85:0.15:0.15 | 15 | 2 |
| HSPC:Chol:HPG 1.85:1:0.15 | 4 | 1 |

EXAMPLE 9

Effect of Charged Lipid Components on Blood/RES Ratios in PEG-PE Liposomes

PEG-PE composed of methoxy PEG, molecular weight 1900 and was derivatized DSPE as described in Example 2. The PEG-PE lipids were formulated with lipids selected from among egg PG (PG), partially hydrogenated egg PC (PHEPC), and cholesterol (Chol), as indicated in the FIG. 7. The two formulations shown in the figure contained about 4.7 mole percent (triangles) or 14 mole percent (circles) PG. The lipids were prepared as MLV's, sized to 0.1 micron as in Example 4.

The percent of injected liposome dose present 0.25, 1, 2, 4, and 24 hours after injection re plotted for both formulations in FIG. 7. As seen, the percent PG in the composition had little or no effect on liposome retention in the bloodstream. The rate of loss of encapsulated marker seen is also similar to that observed for similarly prepared liposomes containing no PG.

EXAMPLE 10

Effect of Liposome Size on Blood Lifetime

PEG-DSPE, prepared as above with PEG-1900, was formulated with partially hydrogenated egg PC (PHEPC), and cholesterol (Chol), at a mole ratio of 0.15: 1.85: 1. The liposomes were sized by extrusion through 0.25, 0.15 or 0.1 micron polycarbonate filters, to produce liposome sizes of about 0.4, 0.2, and 0.1 microns, respectively. Non-encapsulated $^3$H-inulin was removed by gel filtration.

Each of the three liposome were injected intravenously, and the percent of injected liposome marker in the blood was measured at 1, 2, 3, 4, and 24 hours, with the results shown in FIG. 10. All three formulations show long blood half-lives, as evidence by at least bout 10% liposome marker remaining after 24 hours. The 0.1 micron formulation (solid squares) is longer lived than the 0.2 micron formulation (solid circles) which is in turn longer lived than the 0.4 micron formulation.

EXAMPLE 11

Effect of Other Hydrophilic Polymers on Blood Lifetime

Polylactic acid-DSPE or polyglycolic acid-DSPE, prepared as above, was formulated with lipids selected from among hydrogenated soy PC (HSPC), and cholesterol (Chol), at a weight ratio of either 2:3.5:1 or 1:3.5:1. The liposomes were sized by extrusion through a 0.1 micron polycarbonate filter. The liposomes were labeled by $^{67}$Ga-DF as described in Example 5.

These liposome formulations were injected intravenously, and the percent of injected liposome marker in the blood was measured at 1, 2, 3, 4, and 24 hours, with the results shown in FIG. 11. When normalized at 15 minutes, about 3.9% of the liposome marker was present after 24 hours with polylactic acid-DSPE (solid squares). An average value of about 6% of the liposome marker was present after 24 hours after with polyglycolic acid-DSPE (open triangles). This compares with less than 1% remaining for similarly prepared liposomes without the hydrophilic polymers.

EXAMPLE 12

Plasma Kinetics of PEG-Coated and Uncoated Liposomes

PEG-PE composed of methoxy PEG, molecular weight 1900 and distearyl PE (DSPE) was prepared as in Example 2. The PEG-PE lipids were formulated with PHEPC, and cholesterol, in a mole ratio of 0.15:1.85:1. A second lipid mixture contained the same lipids, but without PEG-PE. Liposomes were prepared from the two lipid mixtures as described in Example 5, by lipid hydration in the presence of DF followed by sizing to 0.1 micron, removal of non-entrapped DF by gel filtration, and Ga labeling as described in Example 5. Both compositions contained 10 $\mu$M lipid/ml in 0.15M NaCl, 0.5 mM desferal.

The two liposome compositions (0.4 ml) were injected IV in animals, as described in Example 6. At time 0.25, 1, 3 or 5, and 24 hours after injection, blood samples were removed and assayed for amount inulin remaining in the blood, expressed as a percentage of the amount measured immediately after injection. The results are shown in FIG. 9. As seen, the PEG-coated liposomes have a blood halflife of about 11 hours, and nearly 30% of the injected material is present in the blood after 24 hours. By contrast, uncoated liposomes showed a halflife in the blood of less than 1 hour. At 24 hours, the amount of injected material was undetectable.

EXAMPLE 13

Treatment with Free Vasopressin

Male adult rats of the Brattleboro strain, congenitally deficient for VP (Valtin and Schroeder, 1964), were acclimated to metabolic cages for at least three days before treatment. In most experiments, anesthesia was induced using a mixture of Nitrous oxide 2100 cc/min, oxygen 400 cc/min, and 5% Isoflurane (Aerrane). Anesthesia was maintained throughout surgery with the same gas mixture but with a reduced percentage of isoflurane (2%). In other experiments, inhaled ethyl ether was used for the anesthetic.

A. Surgery

The neck and ventral sides of both hindlimbs were shaved. A small incision was made at the midpoint between the ears at the neck to allow the cannula to be externalized out the neck. The rat was placed on its back and stabilized. An incision was made on the ventral hindlimb at the inguinal area, and fascia was tweezed apart to expose the femoral vascular complex. Further blunt dissection isolated the femoral vein or artery. For the vein, blood flow was occluded by passing a 3—0 silk tie (Davis-Geck, Danbury, Conn.) beneath the vessel distally and applying tension to the vein while clamping the vessel proximally with a bulldog clamp. This allowed the vein to become distended and easier to cut. Using small scissors, the vein was nicked and a bevelled 6-inch section of polyethylene catheter tubing (PE—50 Clay-Adams) filled with normal saline (0.9%) or 5% dextrose was inserted into the vein. Correct placement was verified by venous drawback and flush using a 1 cc syringe. The catheter was anchored loosely to the vein by passing a small tie under the vessel and knotting it around the cannula.

B. Dose Administration

Once animals had been surgically prepared, 150–1000 $\mu$l of test solution was administered intravenously. The dose volume administered was adjusted to give the desired total amount of vasopressin, for example 0.2, 0.8, and 3 $\mu$g of aqueous vasopressin. The venous catheter was then removed, the femoral vein was tied off, and both leg incisions were closed. The animals were allowed to regain consciousness.

C. Urine Production Studies

After a control period during which the rats showed typical symptoms of diabetes insipidus and the urine volume was well established, the animals were weighed and anesthetized with inhaled anesthesia. The femoral vein was cannulated and the dose administered by the surgical procedures described. The animals were maintained in metabolic cages and the urine was collected over the course of several days to several weeks after dose administration. The urine volume was determined hourly immediately after dose administration and thereafter at least twice each day.

FIG. 12 shows the percent predosage urine flow in animals treated with saline (open circles) or 0.2 $\mu$g (solid squares) 0.8 $\mu$g (solid triangles), and 2 $\mu$g (solid circles) vasopressin solution. At day 1 after drug administration, urine production showed a dose-dependent drop. At day 2 and thereafter, urine production was substantially back to control levels.

EXAMPLE 14

Treatment with PEG-Liposomal Vasopressin

Large unilamellar liposomes were prepared according to the reverse phase evaporation procedure (Szoka and Papahadjopoulos, 1978). The lipid composition used in preparing the liposomes was PEG-DSPE, PC, sphingomyelin, and cholesterol, in a mole ratio 0.2:1:1:1. Lipid mixtures for a 1 ml final volume of liposomes with a phospholipid concentration of 10 $\mu$mol/ml were dissolved in chloroform and evaporated to dryness under reduced pressure. After residual solvent was removed under high vacuum for 1 hour the mixture was dissolved in ethyl ether freshly washed with phosphate buffer at pH 7. Then, 0.34 ml of aqueous buffer (5 mM Tris, 100 mM NaCl, 0.1 mM EDTA) containing sufficient arginine vasopressin to give a final drug concentration of 510 $\mu$g/ml was added to the lipids in ether. A trace amount of $^3$H-labeled vasopressin was added to the vasopressin solution for determination of protein concentrations. Then the ether was removed by controlled rotoevaporation, and additional drug-free buffer added to give a 1 ml solution immediately after gel dispersion. The vasopressin content of the resulting liposomes was determined by separating free from liposome-bound by gel filtration on Bio-Gel A15.

The liposomes were extruded through 0.4 $\mu$m Nuclepore filters (Olsen et al., 1979) and particle size distribution measured by dynamic light scattering with a Nicomp model 200. Mean diameter ranged between 0.2 $\mu$m and 0.5 $\mu$m and showed a low polydispersity. Unbound vasopressin was removed by dialysis and monitored by gel chromatography as above.

PEG-liposome preparations from above were administered intravenously to rats prepared as in Example 13, at liposomal doses 2 $\mu$g (solid squares) 8 $\mu$g (solid triangles), and 24 $\mu$g (closed circles) vasopressin solution.

Percent predosage urine flow was measured as above, with the results shown in FIG. 13. The data show substantially the same dose-dependent depression in urine production in the first day after drug administration, presumably resulting predominantly from non-entrapped vasopressin in the liposome formulations. In contrast to free peptide administration, however, all three formulation produced a significant inhibition in urine production with respect to control (open circles) over a 2-8 day period after liposome administration.

EXAMPLE 15

Treatment with PEG-Liposomal Vasopressin: Effect of Liposome Cholesterol Concentration Large unilamellar liposomes were prepared as in Example 14, with liposomes containing either 33, 16, or 0 mole percent cholesterol. Vasopressin encapsulation, liposome sizing, and free peptide removal was carried out as in Example 14.

The three PEG-liposome preparations were administered intravenously to rats prepared as in Example 13, at liposomal doses giving 8 μg vasopressin, and the percent predosage urine production was measured over a 9 day period following liposome administration. The results are shown in FIG. 14, for saline control (open circles) and PEG-liposomes with 0 (solid squares), 16 (solid triangles), and 33 (solid circles) mole percent cholesterol.

The day-1 response shows a marked dependence on percent cholesterol, with the greatest effect on urine flow being produced in liposomes with the lowest mole ratio of cholesterol. This result is consistent with in vitro stability studies of vasopressin release from PEG-liposomes in serum: In the presence of serum, little release of vasopressin was seen in liposomes containing greater than 30 mole percent cholesterol. By contrast, formulations containing reduced amounts of cholesterol showed increasingly higher release rates of encapsulated peptide. Thus, it would appear that the significantly higher diuretic effect seen after 1 day with low and no cholesterol formulations is due to the presence of free peptide released from the liposomes in serum.

Interestingly, all three formulations produced a marked, and substantially similar diuretic effect over a 2-8 day period following liposome drug administration, as was seen in the method described in Example 14.

EXAMPLE 16

Blood Clearance Kinetics of M-CSF from PEG-Liposomes

A lipid film containing PEG-DSPE, PHEPC IV-40, cholesterol, and α-tocopherol, in a mole ratio 5:61:33:1, was hydrated with distilled water, and the resulting MLVs were sonicated for 30 minutes to form SUVs. M-CSF was concentrated and a portion of the protein was labeled with U125I-iodine.

Equal volumes (2 ml) of the protein solution and SUVs were mixed, and the mixture was frozen in an acetone/dry bath, and lyophilized overnight. The dried material was rehydrated in 0.8 ml of distilled water, and the resulting liposome suspension was extruded 1 time through a 0.4μ polycarbonate filter, and 3 times through a 0.2μ filter. The sized liposomes were diluted to 10 ml in distilled water, washed washed two times with high speed centrifugation, and the washed pellet was resuspended in 0.9 μl of sterile buffer, to a final concentration of 40 μmol lipid/ml and between 0.5 and 1.25 mg protein/ml.

PEG-liposome preparations from above were administered intravenously to animals as in Example 6, and the blood levels of M-CSF were measured at 1, 2, 4, and 24 hours after rats prepared as in Example 14. Similar measurements were made for an equivalent amount of M-CSF administered in solution form. The plasma kinetics for the PEG-liposome formulation containing 30 mole percent cholesterol are shown in FIG. 15. The data show rapid clearance of free protein (solid triangles) with less than 1% protein remaining in the blood at 24 hours, compared with about 8% for liposome-associated protein (solid circles). Percent liposomes remaining in the bloodstream, as judged by percent lipid marker, was slightly greater than 10%. A comparison of the clearance of rates of the lipid and protein markers indicates that about 20% of the protein marker was released from the liposomes by 24 hours post injection.

The plasma kinetics obtained with cholesterol-free PEG-liposomes is shown in FIG. 16. Percent liposomes remaining after 24 hours was about 8.5 (solid triangles) compared with about 4.5% for liposome-associated M-CSF. The results indicated that about 40-50% of the originally encapsulated protein leaked from the liposomes in the 24-hour period post injection.

The radioactive counts in the liposome lipid marker and in the encapsulated protein were normalized to 100% initial values, and the percent injected dose released into the bloodstream over time was then determined from the difference between the normalized protein and normalized liposome marker radioactivity levels. A plot of the calculated values of percent protein released at 1, 2, 4, and 24 hours post injection is shown in FIG. 17.

The plot for the cholesterol-free formulation (solid triangles) shows a protein release peak at 2 hours, with a gradual decline in amount released in the 2-24 hour period in the no-cholesterol formulation (solid triangles). The amount of protein released from the liposomes at 24 hours was between 3-4 percent of the total administered.

The plot for the formulation containing 30 mole percent cholesterol (solid circles) shows a gradual increase in release protein release rate over 24 hours. The amount of protein released from the liposomes at 24 hours was about 3 percent of the total administered. Thus, both formulations showed relatively high levels of protein release (3% or greater) at 24 hours.

EXAMPLE 17

Subcutaneously Administered Liposomes

MLVs were prepared by thin-film hydration as described in Example 5. The lipid composition of the thin film was PEG-DSPE, HEPC, and cholesterol, in a mole ratio 0.15:1.85:1. The thin film was hydrated with an aqueous buffer (5 mM Tris, 100 mM NaCl, 0.1 mM EDTA) containing arginine vasopressin at 7.5 mgs/ml. The MLVs were sized by repeated extrusion through a 0.1 micron polycarbonate membrane, and free (non-encapsulated) peptide was removed by gel filtration, as in Example 15. The final concentration of PEG-liposomes in the suspension was 100 μM/ml.

Vasopressin in free form was administered subcutaneously (1 ml) to Brattleboro rats, as in Example 13. The site of subcutaneous injection was the dorsal neck region. The doses administered were 2 μg (solid triangles), 25 μg (solid circles), 50 μg (solid squares), and 100 μg (solid diamonds). The percent of predosage urine flow observed is plotted in FIG. 18A.

Figure 18B:
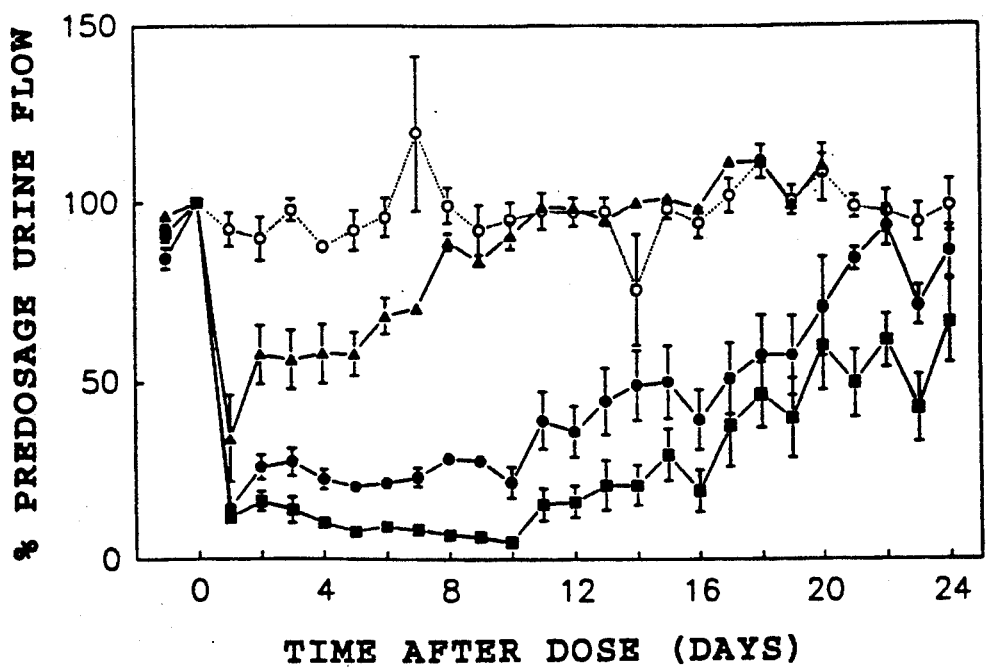
FIG. 18B shows urine flow rates in rats, as a percentage of predosage rate, after surgery and subcutaneous administration of saline (control, open circles) and vasopressin entrapped in PEG-liposomes, in an amount 25 μg (solid triangles), 100 μg (solid, circles), and 400 μg (solid diamonds)

Vasopressin encapsulated in PEG-liposomes, prepared as above, was administered subcutaneously (1 ml) to animals as above. The doses administered were 25 μg (solid triangles), 100 μg (solid circles), and 400 μg (solid squares). The percent of predosage urine flow observed is plotted in FIG. 18B.

Although the invention has been described and illustrated with respect to specific liposome formulations, liposome-entrapped compounds, and treatment methods, it will be apparent that a variety of related compositions, compounds and treatment methods without departing from the invention.

It is claimed:

1. A liposome composition effective to extend, to at least 24 hours, the period of effective activity of a therapeutic compound which can be administered intravenously in a therapeutically effective amount and which is cleared in free form from the bloodstream with a halflife of less than about 4 hours, comprising liposomes (i) composed of vesicle-forming lipids and between 1-20 mole percent of a vesicle-forming lipid derivatized with a polymer selected from the group consisting of polyethyleneglycol, polyacetic acid and polyglycolic acid, and (ii) having a selected mean particle diameter in the size range between about 0.1 to 0.4 microns, and the compound in liposome-entrapped form, for intravenous administration at a dose of the composition which contains an amount of the compound in liposome-entrapped form which is at least three times such therapeutically effective amount.

2. The composition of claim 1, wherein the hydrophilic polymer is polyethyleneglycol having a molecular weight between about 1,000-5,000 daltons.

3. The composition of claim 2, wherein the polymer is derivatized to a phospholipid.

4. The composition of claim 1, wherein the polymer is selected from the group consisting of polyacetic acid and polyglycolic acid.

5. A liposome composition effective to extend, to at least 48 hours, the period of therapeutic activity of a polypeptide which can be administered intravenously in a therapeutically effective amount, which is cleared in free form from the bloodstream with a halflife of less than about 4 hours, and whose therapeutically active blood concentration is in the picogram-nanogram/ml concentration range, comprising liposomes (i) composed of vesicle-forming lipids and between 1-20 mole percent of a vesicle-forming lipid derivitized with a polymer selected from the group consisting of polyethyleneglycol, polyacetic acid and polyglycolic acid, and (ii) having a selected mean particle diameter in the size range between about 0.1 to 0.4 microns, and the polypeptide in liposome-entrapped form, for intravenous administration at a dose of the composition which contains an amount of the polypeptide liposome-entrapped form which is at least three times such therapeutically effective amount.

6. The composition of claim 5, wherein the hydrophilic polymer is polyethyleneglycol having a molecular weight between about 1,000-5,000 daltons.

7. The composition of claim 5, wherein the polypeptide is a peptide hormone which is therapeutically active at a plasma concentration in the picogram/ml range, and the liposome composition is effective to release the hormone in a therapeutically effective dose for a period of at least five days after intravenous administration of the composition.

8. The composition of claim 7, wherein the peptide hormone is vasopressin.

9. The composition of claim 5, wherein the compound is a protein selected from the group consisting of superoxide dismutase, glucocerebrosidase, asparaginase, adenosine deaminase, interferons (alpha, beta, and gamma), interleukin (1,2,3,4,5,6,7), tissue necroses factor (TNF-alpha, beta), colony stimulating factors (-CSF (macrophage), G-CSF (granulocyte), GM-CSF (granulocyte, macrophage), TPA, prourokinase, and urokinase, HIV-1 vaccine, hepatitis B vaccine, malaria vaccine, and melanoma vaccine, erythropoietin (EPO), factor VIII, bone growth factor, fibroblast growth factor, nerve growth factor, platelet-derived growth factor, tumor growth factors (alpha, beta), somatomedin C (IGF-1), and a ribosome inhibitor protein.

10. The composition of claim 9, wherein the protein is macrophage colony stimulating factor.

11. A method of extending, to at least 24 hours, the period of effective activity of a therapeutic compound which can be administered intravenously in a therapeutically effective amount, and which has a halflife in the bloodstream in free form of less than about 4 hours, comprising providing a liposome composition containing liposomes (i) composed of vesicle-forming lipids and between 1-20 mole percent of a vesicle-forming lipid derivitized with ah polymer selected from the group consisting of polyethyleneglycol, polyacetic acid and polyglycolic acid, and (ii) having a selected mean particle diameter in the size range between about 0.1 to 0.4 microns, and the compound at least about 70% in liposome-entrapped form, and administering the liposome composition intravenously to a subject at a dose which contains an amount of the compound which is at least three times such therapeutically effective amount.

12. The method of claim 11, wherein the hydrophilic polymer is polyethyleneglycol having a molecular weight between about 1,000-5,000 daltons.

13. The method of claim 11, wherein the polymer is selected from the group consisting of polylactic acid and polyglycolic acid.

14. The method of claim 11, wherein the compound is a peptide hormone which is therapeutically active at a plasma concentration in the picogram-to-nanogram/ml range, and said administering is effective to release the hormone in a therapeutically effective dose for a period of at least five days.

15. The method of claim 14, wherein the peptide hormone is vasopressin.

16. The method of claim 11, wherein the compound is a protein selected from the group consisting of superoxide dismutase, glucocerebrosidase, asparaginase, adenosine deaminase, interferons (alpha, beta, and gamma), interleukin (1,2,3,4,5,6,7), tissue necroses factor (TNF-alpha, beta), colony stimulating factors (M-CSF (macrophage), G-CSF (granulocyte), GM-CSF (granulocyte, macrophage), TPA, prourokinase, and urokinase, HIV-1 vaccine, erythropoietin (EPO), factor VIII, bone growth factor, fibroblast growth factor, nerve growth factor, platelet-derived growth factor, tumor growth factors (alpha, beta), somatomedin C (IGF-1), and a ribosome inhibitor protein.

17. The method of claim 16, wherein the protein is macrophage colony stimulating factor.

18. A liposome composition effective to extend, to at least one week, the period of effective activity of a therapeutic compound which can be administered in a therapeutically effective amount, comprising liposomes (i) composed of vesicle-forming lipids and between 1-20 mole percent of a vesicle-forming lipid derivitized with a polymer selected from the group consisting of polyethyleneglycol, polyacetic acid and polyglycolic acid, and (ii) having a selected mean particle diameter in the size range between about 0.1 to 0.4 microns, and the compound in liposome-entrapped form, for subcutaneous administration at a dose of the composition which contains an amount of the compound in liposome-entrapped form which is at least ten times such therapeutically effective intravenously administered amount.

19. The composition of claim 18, wherein the compound is a polypeptide selected from the group consisting of superoxide dismutase, glucocerebrosidase, asparaginase, adenosine deaminase, interferons (alpha, beta, and gamma), interleukin (1,2,3,4,5,6,7), tissue necrosis factor (TNF - alpha, beta), colony stimulating factors (M-CSF (macrophage), G-CSF (granulocyte), GM-CSF (granulocyte, macrophage), TPA, prourokinase, and urokinase, HIV-1 vaccine, hepatitis B vaccine, malaria vaccine, and melanoma vaccine, erythropoietin (EPO), factor VIII, bone growth factor, fibroblast growth factor, nerve growth factor, platelet-derived growth factor, tumor growth factors (alpha, beta), somatomedin C (IGF-1), and a ribosome inhibitor protein.

20. The composition of claim 19, wherein the polypeptide is vasopressin.

21. A method of extending, to at least one week, the period of effective activity of a therapeutic compound which can be administered in a therapeutically effective amount, comprising providing a liposome composition containing liposomes (i) composed of vesicle-forming lipids and between 1-20 mole percent of a vesicle-forming lipid derivitized with a polymer selected from the group consisting of polyethyleneglycol, polyacetic acid and polyglycolic acid, and (ii) having a selected mean particle diameter in the size range between about 0.1 to 0.4 microns, and the compound at least about 70% in liposome-entrapped form, and administering the composition subcutaneously to a subject at a dose which contains an amount of the compound in liposome-entrapped form which is at least ten times such therapeutically effective intravenously administered amount.

22. The method of claim 21, wherein the compound is a peptide hormone selected from the group consisting of superoxide dismutase, glucocerebrosidase, asparaginase, adenosine deaminase, interferons (alpha, beta, and gamma), interleukin (1,2,3,4,5,6,7), tissue necroses factor (TNF-alpha, beta), colony stimulating factors (M-CSF (macrophage), G-CSF (granulocyte), GM-CSF (granulocyte, macrophage), TPA, prourokinase, and urokinase, HIV-1 vaccine, hepatitis B vaccine, malaria vaccine, and melanoma vaccine, erythropoietin (EPO), factor VIII, bone growth factor, fibroblast growth factor, nerve growth factor, platelet-derived growth factor, tumor growth factors (alpha, beta), somatomedin C (IGF-1), and a ribosome inhibitor protein.

23. The method of claim 22, wherein the polypeptide is vasopressin.

24. A liposome composition composed of vesicle-forming lipids and a vesicle-forming lipid derivatized with a hydrophilic polymer selected from the group consisting of polylactic acid and polyglycolic acid.

25. A lipid composition composed of a vesicle-forming lipid having a polar head group, and a polylactic acid moiety derivatized to said head group.

26. A lipid composition composed of a vesicle-forming lipid having a polar head group, and a polyglycolic acid moiety derivatized to said head group.

* * * * *